(12) United States Patent
Tegels et al.

(10) Patent No.: US 11,096,783 B2
(45) Date of Patent: Aug. 24, 2021

(54) APPARATUS AND METHODS FOR DELIVERY OF TRANSCATHETER PROSTHETIC VALVES

(71) Applicant: Tendyne Holdings, Inc., St. Paul, MN (US)

(72) Inventors: Zachary J. Tegels, Minneapolis, MN (US); Robert M. Vidlund, Forest Lake, MN (US)

(73) Assignee: Tendyne Holdings, Inc., St. Paul, MN (US)

( * ) Notice: Subject to any disclaimer, the term of this patent is extended or adjusted under 35 U.S.C. 154(b) by 300 days.

(21) Appl. No.: 16/385,180

(22) Filed: Apr. 16, 2019

(65) Prior Publication Data

US 2019/0240014 A1 Aug. 8, 2019

Related U.S. Application Data

(63) Continuation of application No. 15/388,571, filed on Dec. 22, 2016, now Pat. No. 10,363,135, which is a
(Continued)

(51) Int. Cl.
*A61F 2/24* (2006.01)
*A61F 2/95* (2013.01)
(Continued)

(52) U.S. Cl.
CPC .......... *A61F 2/2436* (2013.01); *A61F 2/2418* (2013.01); *A61F 2/2427* (2013.01);
(Continued)

(58) Field of Classification Search
CPC ................. A61F 2/2427; A61F 2/2436; A61F 2250/0039; A61F 2002/9517;
(Continued)

(56) References Cited

U.S. PATENT DOCUMENTS 2,697,008 A 12/1954 Ross
3,409,013 A 11/1968 Berry
(Continued)

FOREIGN PATENT DOCUMENTS

CN 1486161 A 3/2004
CN 1961845 A 5/2007
(Continued)

OTHER PUBLICATIONS

US 9,155,620 B2, 10/2015, Gross et al. (withdrawn)
(Continued)

*Primary Examiner* — Julian W Woo
(74) *Attorney, Agent, or Firm* — Lerner, David, Littenberg, Krumholz & Mentlik, LLP

(57) ABSTRACT

In some embodiments, an apparatus includes a catheter assembly and a handle assembly that can be removably coupled to the catheter assembly. A valve holding tube defines a lumen configured to receive a prosthetic mitral valve in a compressed configuration and can be removably coupled to a distal end portion of the handle assembly. The valve holding tube can be received within a hub of the catheter assembly when coupled to the handle assembly. The actuator when actuated is configured to cause the tensioning unit to travel along a traveler strap of the catheter assembly moving the handle assembly distally such that a distal end of an elongate shaft of the handle assembly moves the prosthetic mitral valve distally out of the valve holding tube and out a distal end of the sheath such that the prosthetic mitral valve is free to move to a biased expanded configuration.

20 Claims, 20 Drawing Sheets

Related U.S. Application Data continuation of application No. 14/527,382, filed on Oct. 29, 2014, now Pat. No. 9,526,611.

(60) Provisional application No. 61/896,664, filed on Oct. 29, 2013.

(51) Int. Cl.
*A61B 50/00* (2016.01)
*A61B 50/30* (2016.01)
*A61F 2/00* (2006.01)

(52) U.S. Cl.
CPC .............. *A61B 50/00* (2016.02); *A61B 50/30* (2016.02); *A61F 2/0095* (2013.01); *A61F 2/95* (2013.01); *A61F 2/9517* (2020.05); *A61F 2230/0067* (2013.01); *A61F 2250/0039* (2013.01); *A61F 2250/0062* (2013.01)

(58) Field of Classification Search
CPC ..... A61F 2230/0067; A61F 2250/0062; A61B 50/30; A61B 50/00
See application file for complete search history.

(56) References Cited

U.S. PATENT DOCUMENTS

| | | | |
|---|---|---|---|
| 3,472,230 | A | 10/1969 | Fogarty et al. |
| 3,476,101 | A | 11/1969 | Ross |
| 3,548,417 | A | 12/1970 | Kischer |
| 3,587,115 | A | 6/1971 | Shiley |
| 3,657,744 | A | 4/1972 | Ersek |
| 3,671,979 | A | 6/1972 | Moulopoulos |
| 3,714,671 | A | 2/1973 | Edwards et al. |
| 3,755,823 | A | 9/1973 | Hancock |
| 3,976,079 | A | 8/1976 | Samuels et al. |
| 4,003,382 | A | 1/1977 | Dyke |
| 4,035,849 | A | 7/1977 | Angell et al. |
| 4,056,854 | A | 11/1977 | Boretos et al. |
| 4,073,438 | A | 2/1978 | Meyer |
| 4,106,129 | A | 8/1978 | Carpentier et al. |
| 4,222,126 | A | 9/1980 | Boretos et al. |
| 4,265,694 | A | 5/1981 | Boretos et al. |
| 4,297,749 | A | 11/1981 | Davis et al. |
| 4,339,831 | A | 7/1982 | Johnson |
| 4,343,048 | A | 8/1982 | Ross et al. |
| 4,345,340 | A | 8/1982 | Rosen |
| 4,373,216 | A | 2/1983 | Klawitter |
| 4,406,022 | A | 9/1983 | Roy |
| 4,470,157 | A | 9/1984 | Love |
| 4,490,859 | A | 1/1985 | Black et al. |
| 4,535,483 | A | 8/1985 | Klawitter et al. |
| 4,574,803 | A | 3/1986 | Storz |
| 4,585,705 | A | 4/1986 | Broderick et al. |
| 4,592,340 | A | 6/1986 | Boyles |
| 4,605,407 | A | 8/1986 | Black et al. |
| 4,612,011 | A | 9/1986 | Kautzky |
| 4,626,255 | A | 12/1986 | Reichart et al. |
| 4,638,886 | A | 1/1987 | Marietta |
| 4,643,732 | A | 2/1987 | Pietsch et al. |
| 4,655,771 | A | 4/1987 | Wallsten |
| 4,692,164 | A | 9/1987 | Dzemeshkevich et al. |
| 4,733,665 | A | 3/1988 | Palmaz |
| 4,759,758 | A | 7/1988 | Gabbay |
| 4,762,128 | A | 8/1988 | Rosenbluth |
| 4,777,951 | A | 10/1988 | Cribier et al. |
| 4,787,899 | A | 11/1988 | Lazarus |
| 4,787,901 | A | 11/1988 | Baykut |
| 4,796,629 | A | 1/1989 | Grayzel |
| 4,824,180 | A | 4/1989 | Levrai |
| 4,829,990 | A | 5/1989 | Thuroff et al. |
| 4,830,117 | A | 5/1989 | Capasso |
| 4,851,001 | A | 7/1989 | Taheri |
| 4,856,516 | A | 8/1989 | Hillstead |
| 4,878,495 | A | 11/1989 | Grayzel |
| 4,878,906 | A | 11/1989 | Lindemann et al. |
| 4,883,458 | A | 11/1989 | Shiber |
| 4,922,905 | A | 5/1990 | Strecker |
| 4,923,013 | A | 5/1990 | De Gennaro |
| 4,960,424 | A | 10/1990 | Grooters |
| 4,966,604 | A | 10/1990 | Reiss |
| 4,979,939 | A | 12/1990 | Shiber |
| 4,986,830 | A | 1/1991 | Owens et al. |
| 4,994,077 | A | 2/1991 | Dobben |
| 4,996,873 | A | 3/1991 | Takeuchi |
| 5,007,896 | A | 4/1991 | Shiber |
| 5,026,366 | A | 6/1991 | Leckrone |
| 5,032,128 | A | 7/1991 | Alonso |
| 5,037,434 | A | 8/1991 | Lane |
| 5,047,041 | A | 9/1991 | Samuels |
| 5,059,177 | A | 10/1991 | Towne et al. |
| 5,064,435 | A | 11/1991 | Porter |
| 5,080,668 | A | 1/1992 | Bolz et al. |
| 5,085,635 | A | 2/1992 | Cragg |
| 5,089,015 | A | 2/1992 | Ross |
| 5,152,771 | A | 10/1992 | Sabbaghian et al. |
| 5,163,953 | A | 11/1992 | Vince |
| 5,167,628 | A | 12/1992 | Boyles |
| 5,192,297 | A | 3/1993 | Hull |
| 5,201,880 | A | 4/1993 | Wright et al. |
| 5,266,073 | A | 11/1993 | Wall |
| 5,282,847 | A | 2/1994 | Trescony et al. |
| 5,295,958 | A | 3/1994 | Shturman |
| 5,306,296 | A | 4/1994 | Wright et al. |
| 5,332,402 | A | 7/1994 | Teitelbaum |
| 5,336,616 | A | 8/1994 | Livesey et al. |
| 5,344,442 | A | 9/1994 | Deac |
| 5,360,444 | A | 11/1994 | Kusuhara |
| 5,364,407 | A | 11/1994 | Poll |
| 5,370,685 | A | 12/1994 | Stevens |
| 5,397,351 | A | 3/1995 | Pavcnik et al. |
| 5,411,055 | A | 5/1995 | Kane |
| 5,411,552 | A | 5/1995 | Andersen et al. |
| 5,415,667 | A | 5/1995 | Frater |
| 5,443,446 | A | 8/1995 | Shturman |
| 5,480,424 | A | 1/1996 | Cox |
| 5,500,014 | A | 3/1996 | Quijano et al. |
| 5,545,209 | A | 8/1996 | Roberts et al. |
| 5,545,214 | A | 8/1996 | Stevens |
| 5,549,665 | A | 8/1996 | Vesely et al. |
| 5,554,184 | A | 9/1996 | Machiraju |
| 5,554,185 | A | 9/1996 | Block et al. |
| 5,571,175 | A | 11/1996 | Vanney et al. |
| 5,591,185 | A | 1/1997 | Kilmer et al. |
| 5,607,462 | A | 3/1997 | Imran |
| 5,607,464 | A | 3/1997 | Trescony et al. |
| 5,609,626 | A | 3/1997 | Quijano et al. |
| 5,639,274 | A | 6/1997 | Fischell et al. |
| 5,662,704 | A | 9/1997 | Gross |
| 5,665,115 | A | 9/1997 | Cragg |
| 5,674,279 | A | 10/1997 | Wright et al. |
| 5,697,905 | A | 12/1997 | d'Ambrosio |
| 5,702,368 | A | 12/1997 | Stevens et al. |
| 5,716,417 | A | 2/1998 | Girard et al. |
| 5,728,068 | A | 3/1998 | Leone et al. |
| 5,728,151 | A | 3/1998 | Garrison et al. |
| 5,741,333 | A | 4/1998 | Frid |
| 5,749,890 | A | 5/1998 | Shaknovich |
| 5,756,476 | A | 5/1998 | Epstein et al. |
| 5,769,812 | A | 6/1998 | Stevens et al. |
| 5,792,179 | A | 8/1998 | Sideris |
| 5,800,508 | A | 9/1998 | Goicoechea et al. |
| 5,833,673 | A | 11/1998 | Ockuly et al. |
| 5,840,081 | A | 11/1998 | Andersen et al. |
| 5,855,597 | A | 1/1999 | Jayaraman |
| 5,855,601 | A | 1/1999 | Bessler et al. |
| 5,855,602 | A | 1/1999 | Angell |
| 5,904,697 | A | 5/1999 | Gifford, III et al. |
| 5,925,063 | A | 7/1999 | Khosravi |
| 5,957,949 | A | 9/1999 | Leonhardt et al. |
| 5,968,052 | A | 10/1999 | Sullivan, III et al. |
| 5,968,068 | A | 10/1999 | Dehdashtian et al. |
| 5,972,030 | A | 10/1999 | Garrison et al. |
| 5,993,481 | A | 11/1999 | Marcade et al. |

(56) References Cited

U.S. PATENT DOCUMENTS

| | | |
|---|---|---|
| 6,027,525 A | 2/2000 | Suh et al. |
| 6,042,607 A | 3/2000 | Williamson, IV et al. |
| 6,045,497 A | 4/2000 | Schweich, Jr. et al. |
| 6,063,112 A | 5/2000 | Sgro |
| 6,077,214 A | 6/2000 | Mortier et al. |
| 6,099,508 A | 8/2000 | Bousquet |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,183,411 B1 | 2/2001 | Mortier et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,260,552 B1 | 7/2001 | Mortier et al. |
| 6,261,222 B1 | 7/2001 | Schweich, Jr. et al. |
| 6,264,602 B1 | 7/2001 | Mortier et al. |
| 6,287,339 B1 | 9/2001 | Vazquez et al. |
| 6,299,637 B1 | 10/2001 | Shaolian et al. |
| 6,302,906 B1 | 10/2001 | Goicoechea et al. |
| 6,312,465 B1 | 11/2001 | Griffin et al. |
| 6,332,893 B1 | 12/2001 | Mortier et al. |
| 6,350,277 B1 | 2/2002 | Kocur |
| 6,358,277 B1 | 3/2002 | Duran |
| 6,379,372 B1 | 4/2002 | Dehdashtian et al. |
| 6,402,679 B1 | 6/2002 | Mortier et al. |
| 6,402,680 B2 | 6/2002 | Mortier et al. |
| 6,402,781 B1 | 6/2002 | Langberg et al. |
| 6,406,420 B1 | 6/2002 | McCarthy et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,537,198 B1 | 3/2003 | Vidlund et al. |
| 6,540,782 B1 | 4/2003 | Snyders |
| 6,569,196 B1 | 5/2003 | Vesely |
| 6,575,252 B2 | 6/2003 | Reed |
| 6,582,462 B1 | 6/2003 | Andersen et al. |
| 6,605,112 B1 | 8/2003 | Moll et al. |
| 6,616,684 B1 | 9/2003 | Vidlund et al. |
| 6,622,730 B2 | 9/2003 | Ekvall et al. |
| 6,629,534 B1 | 10/2003 | St. Goar et al. |
| 6,629,921 B1 | 10/2003 | Schweich, Jr. et al. |
| 6,648,077 B2 | 11/2003 | Hoffman |
| 6,648,921 B2 | 11/2003 | Anderson et al. |
| 6,652,578 B2 | 11/2003 | Bailey et al. |
| 6,669,724 B2 | 12/2003 | Park et al. |
| 6,706,065 B2 | 3/2004 | Langberg et al. |
| 6,709,456 B2 | 3/2004 | Langberg et al. |
| 6,723,038 B1 | 4/2004 | Schroeder et al. |
| 6,726,715 B2 | 4/2004 | Sutherland |
| 6,730,118 B2 | 5/2004 | Spenser et al. |
| 6,733,525 B2 | 5/2004 | Yang et al. |
| 6,740,105 B2 | 5/2004 | Yodfat et al. |
| 6,746,401 B2 | 6/2004 | Panescu |
| 6,746,471 B2 | 6/2004 | Mortier et al. |
| 6,752,813 B2 | 6/2004 | Goldfarb et al. |
| 6,764,510 B2 | 7/2004 | Vidlund et al. |
| 6,797,002 B2 | 9/2004 | Spence et al. |
| 6,810,882 B2 | 11/2004 | Langberg et al. |
| 6,830,584 B1 | 12/2004 | Seguin |
| 6,854,668 B2 | 2/2005 | Wancho et al. |
| 6,855,144 B2 | 2/2005 | Lesh |
| 6,858,001 B1 | 2/2005 | Aboul-Hosn |
| 6,890,353 B2 | 5/2005 | Cohn et al. |
| 6,893,460 B2 | 5/2005 | Spenser et al. |
| 6,896,690 B1 | 5/2005 | Lambrecht et al. |
| 6,908,424 B2 | 6/2005 | Mortier et al. |
| 6,908,481 B2 | 6/2005 | Cribier |
| 6,936,067 B2 | 8/2005 | Buchanan |
| 6,945,996 B2 | 9/2005 | Sedransk |
| 6,955,175 B2 | 10/2005 | Stevens et al. |
| 6,974,476 B2 | 12/2005 | McGuckin, Jr. et al. |
| 6,976,543 B1 | 12/2005 | Fischer |
| 6,997,950 B2 | 2/2006 | Chawla |
| 7,018,406 B2 | 3/2006 | Seguin et al. |
| 7,018,408 B2 | 3/2006 | Bailey et al. |
| 7,044,905 B2 | 5/2006 | Vidlund et al. |
| 7,060,021 B1 | 6/2006 | Wilk |
| 7,077,862 B2 | 7/2006 | Vidlund et al. |
| 7,087,064 B1 | 8/2006 | Hyde |
| 7,100,614 B2 | 9/2006 | Stevens et al. |
| 7,101,395 B2 | 9/2006 | Tremulis et al. |
| 7,108,717 B2 | 9/2006 | Freidberg |
| 7,112,219 B2 | 9/2006 | Vidlund et al. |
| 7,115,141 B2 | 10/2006 | Menz et al. |
| 7,141,064 B2 | 11/2006 | Scott et al. |
| 7,175,656 B2 | 2/2007 | Khairkhahan |
| 7,198,646 B2 | 4/2007 | Figulla et al. |
| 7,201,772 B2 | 4/2007 | Schwammenthal et al. |
| 7,247,134 B2 | 7/2007 | Vidlund et al. |
| 7,252,682 B2 | 8/2007 | Seguin |
| 7,267,686 B2 | 9/2007 | DiMatteo et al. |
| 7,275,604 B1 | 10/2007 | Wall |
| 7,276,078 B2 | 10/2007 | Spenser et al. |
| 7,276,084 B2 | 10/2007 | Yang et al. |
| 7,316,706 B2 | 1/2008 | Bloom et al. |
| 7,318,278 B2 | 1/2008 | Zhang et al. |
| 7,326,236 B2 | 2/2008 | Andreas et al. |
| 7,329,278 B2 | 2/2008 | Seguin et al. |
| 7,331,991 B2 | 2/2008 | Kheradvar et al. |
| 7,335,213 B1 | 2/2008 | Hyde et al. |
| 7,374,571 B2 | 5/2008 | Pease et al. |
| 7,377,941 B2 | 5/2008 | Rhee et al. |
| 7,381,210 B2 | 6/2008 | Zarbatany et al. |
| 7,381,218 B2 | 6/2008 | Schreck |
| 7,393,360 B2 | 7/2008 | Spenser et al. |
| 7,404,824 B1 | 7/2008 | Webler et al. |
| 7,416,554 B2 | 8/2008 | Lam et al. |
| 7,422,072 B2 | 9/2008 | Dade |
| 7,429,269 B2 | 9/2008 | Schwammenthal et al. |
| 7,442,204 B2 | 10/2008 | Schwammenthal et al. |
| 7,445,631 B2 | 11/2008 | Salahieh et al. |
| 7,462,191 B2 | 12/2008 | Spenser et al. |
| 7,470,285 B2 | 12/2008 | Nugent et al. |
| 7,500,989 B2 | 3/2009 | Solem et al. |
| 7,503,931 B2 | 3/2009 | Kowalsky et al. |
| 7,510,572 B2 | 3/2009 | Gabbay |
| 7,510,575 B2 | 3/2009 | Spenser et al. |
| 7,513,908 B2 | 4/2009 | Lattouf |
| 7,524,330 B2 | 4/2009 | Berreklouw |
| 7,527,647 B2 | 5/2009 | Spence |
| 7,534,260 B2 | 5/2009 | Lattouf |
| 7,556,646 B2 | 7/2009 | Yang et al. |
| 7,579,381 B2 | 8/2009 | Dove |
| 7,585,321 B2 | 9/2009 | Cribier |
| 7,591,847 B2 | 9/2009 | Navia et al. |
| 7,618,446 B2 | 11/2009 | Andersen et al. |
| 7,618,447 B2 | 11/2009 | Case et al. |
| 7,621,948 B2 | 11/2009 | Herrmann et al. |
| 7,632,304 B2 | 12/2009 | Park |
| 7,632,308 B2 | 12/2009 | Loulmet |
| 7,635,386 B1 | 12/2009 | Gammie |
| 7,674,222 B2 | 3/2010 | Nikolic et al. |
| 7,674,286 B2 | 3/2010 | Alfieri et al. |
| 7,695,510 B2 | 4/2010 | Bloom et al. |
| 7,708,775 B2 | 5/2010 | Rowe et al. |
| 7,748,389 B2 | 7/2010 | Salahieh et al. |
| 7,766,961 B2 | 8/2010 | Patel et al. |
| 7,789,909 B2 | 9/2010 | Andersen et al. |
| 7,803,168 B2 | 9/2010 | Gifford et al. |
| 7,803,184 B2 | 9/2010 | McGuckin, Jr. et al. |
| 7,803,185 B2 | 9/2010 | Gabbay |
| 7,806,928 B2 | 10/2010 | Rowe et al. |
| 7,837,727 B2 | 11/2010 | Goetz et al. |
| 7,854,762 B2 | 12/2010 | Speziali et al. |
| 7,892,281 B2 | 2/2011 | Seguin et al. |
| 7,896,915 B2 | 3/2011 | Guyenot et al. |

(56) References Cited

U.S. PATENT DOCUMENTS

| | | |
|---|---|---|
| 7,901,454 B2 | 3/2011 | Kapadia et al. |
| 7,927,370 B2 | 4/2011 | Webler et al. |
| 7,931,630 B2 | 4/2011 | Nishtala et al. |
| 7,942,928 B2 | 5/2011 | Webler et al. |
| 7,955,247 B2 | 6/2011 | Levine et al. |
| 7,955,385 B2 | 6/2011 | Crittenden |
| 7,972,378 B2 | 7/2011 | Tabor et al. |
| 7,988,727 B2 | 8/2011 | Santamore et al. |
| 7,993,394 B2 | 8/2011 | Hariton et al. |
| 8,007,992 B2 | 8/2011 | Tian et al. |
| 8,029,556 B2 | 10/2011 | Rowe |
| 8,043,368 B2 | 10/2011 | Crabtree |
| 8,052,749 B2 | 11/2011 | Salahieh et al. |
| 8,052,750 B2 | 11/2011 | Tuval et al. |
| 8,052,751 B2 | 11/2011 | Aklog et al. |
| 8,062,355 B2 | 11/2011 | Figulla et al. |
| 8,062,359 B2 | 11/2011 | Marquez et al. |
| 8,070,802 B2 | 12/2011 | Lamphere et al. |
| 8,109,996 B2 | 2/2012 | Stacchino et al. |
| 8,142,495 B2 | 3/2012 | Hasenkam et al. |
| 8,152,821 B2 | 4/2012 | Gambale et al. |
| 8,157,810 B2 | 4/2012 | Case et al. |
| 8,167,932 B2 | 5/2012 | Bourang et al. |
| 8,167,934 B2 | 5/2012 | Styrc et al. |
| 8,187,299 B2 | 5/2012 | Goldfarb et al. |
| 8,206,439 B2 | 6/2012 | Gomez Duran |
| 8,216,301 B2 | 7/2012 | Bonhoeffer et al. |
| 8,226,711 B2 | 7/2012 | Mortier et al. |
| 8,236,045 B2 | 8/2012 | Benichou et al. |
| 8,241,274 B2 | 8/2012 | Keogh et al. |
| 8,252,051 B2 | 8/2012 | Chau et al. |
| 8,303,653 B2 | 11/2012 | Bonhoeffer et al. |
| 8,308,796 B2 | 11/2012 | Lashinski et al. |
| 8,323,334 B2 | 12/2012 | Deem et al. |
| 8,353,955 B2 | 1/2013 | Styrc et al. |
| RE44,075 E | 3/2013 | Williamson et al. |
| 8,449,599 B2 | 5/2013 | Chau et al. |
| 8,454,656 B2 | 6/2013 | Tuval |
| 8,470,028 B2 | 6/2013 | Thornton et al. |
| 8,480,730 B2 | 7/2013 | Maurer et al. |
| 8,486,138 B2 | 7/2013 | Vesely |
| 8,506,623 B2 | 8/2013 | Wilson et al. |
| 8,506,624 B2 | 8/2013 | Vidlund et al. |
| 8,578,705 B2 | 11/2013 | Sindano et al. |
| 8,579,913 B2 | 11/2013 | Nielsen |
| 8,591,573 B2 | 11/2013 | Barone |
| 8,591,576 B2 | 11/2013 | Hasenkam et al. |
| 8,597,347 B2 | 12/2013 | Maurer et al. |
| 8,685,086 B2 | 4/2014 | Navia et al. |
| 8,790,394 B2 | 7/2014 | Miller et al. |
| 8,845,717 B2 | 9/2014 | Khairkhahan et al. |
| 8,888,843 B2 | 11/2014 | Khairkhahan et al. |
| 8,900,214 B2 | 12/2014 | Nance et al. |
| 8,900,295 B2 | 12/2014 | Migliazza et al. |
| 8,926,696 B2 | 1/2015 | Cabiri et al. |
| 8,932,342 B2 | 1/2015 | McHugo et al. |
| 8,932,348 B2 | 1/2015 | Salem et al. |
| 8,945,208 B2 | 2/2015 | Jimenez et al. |
| 8,956,407 B2 | 2/2015 | Macoviak et al. |
| 8,979,922 B2 | 3/2015 | Jayasinghe et al. |
| 8,986,376 B2 | 3/2015 | Salem |
| 9,011,522 B2 | 4/2015 | Annest |
| 9,023,099 B2 | 5/2015 | Duffy et al. |
| 9,034,032 B2 | 5/2015 | McLean et al. |
| 9,034,033 B2 | 5/2015 | McLean et al. |
| 9,039,757 B2 | 5/2015 | McLean et al. |
| 9,039,759 B2 | 5/2015 | Alkhatib et al. |
| 9,078,749 B2 | 7/2015 | Lutter et al. |
| 9,084,676 B2 | 7/2015 | Chau et al. |
| 9,095,433 B2 | 8/2015 | Lutter et al. |
| 9,125,742 B2 | 9/2015 | Yoganathan et al. |
| 9,149,357 B2 | 10/2015 | Seguin |
| 9,161,837 B2 | 10/2015 | Kapadia |
| 9,168,137 B2 | 10/2015 | Subramanian et al. |
| 9,232,998 B2 | 1/2016 | Wilson et al. |
| 9,232,999 B2 | 1/2016 | Maurer et al. |
| 9,241,702 B2 | 1/2016 | Maisano et al. |
| 9,254,192 B2 | 2/2016 | Lutter et al. |
| 9,265,608 B2 | 2/2016 | Miller et al. |
| 9,289,295 B2 | 3/2016 | Aklog et al. |
| 9,289,297 B2 | 3/2016 | Wilson et al. |
| 9,345,573 B2 | 5/2016 | Nyuli et al. |
| 9,364,325 B2 | 6/2016 | Alon et al. |
| 9,480,557 B2 | 11/2016 | Pellegrini et al. |
| 9,480,559 B2 | 11/2016 | Vidlund et al. |
| 9,526,611 B2 | 12/2016 | Tegels et al. |
| 9,597,181 B2 | 3/2017 | Christianson et al. |
| 9,610,159 B2 | 4/2017 | Christianson et al. |
| 9,675,454 B2 | 6/2017 | Vidlund et al. |
| 9,730,792 B2 | 8/2017 | Lutter et al. |
| 10,016,275 B2 * | 7/2018 | Nyuli .................. A61F 2/2412 |
| 2001/0018611 A1 | 8/2001 | Salem et al. |
| 2001/0021872 A1 | 9/2001 | Bailey et al. |
| 2001/0025171 A1 | 9/2001 | Mortier et al. |
| 2002/0010427 A1 | 1/2002 | Scarfone et al. |
| 2002/0116054 A1 | 8/2002 | Lundell et al. |
| 2002/0139056 A1 | 10/2002 | Finnell |
| 2002/0151961 A1 | 10/2002 | Lashinski et al. |
| 2002/0161377 A1 | 10/2002 | Rabkin |
| 2002/0173842 A1 | 11/2002 | Buchanan |
| 2003/0010509 A1 | 1/2003 | Hoffman |
| 2003/0036698 A1 | 2/2003 | Kohler et al. |
| 2003/0050694 A1 | 3/2003 | Yang et al. |
| 2003/0078652 A1 | 4/2003 | Sutherland |
| 2003/0100939 A1 | 5/2003 | Yodfat et al. |
| 2003/0105519 A1 | 6/2003 | Fasol et al. |
| 2003/0105520 A1 | 6/2003 | Alferness et al. |
| 2003/0120340 A1 | 6/2003 | Liska et al. |
| 2003/0130731 A1 | 7/2003 | Vidlund et al. |
| 2003/0149476 A1 | 8/2003 | Damm et al. |
| 2003/0212454 A1 | 11/2003 | Scott et al. |
| 2004/0039436 A1 | 2/2004 | Spenser et al. |
| 2004/0049266 A1 | 3/2004 | Anduiza et al. |
| 2004/0064014 A1 | 4/2004 | Melvin et al. |
| 2004/0092858 A1 | 5/2004 | Wilson et al. |
| 2004/0093075 A1 | 5/2004 | Kuehne |
| 2004/0097865 A1 | 5/2004 | Anderson et al. |
| 2004/0127983 A1 | 7/2004 | Mortier et al. |
| 2004/0133263 A1 | 7/2004 | Dusbabek et al. |
| 2004/0147958 A1 | 7/2004 | Lam et al. |
| 2004/0152947 A1 | 8/2004 | Schroeder et al. |
| 2004/0162610 A1 | 8/2004 | Liska et al. |
| 2004/0163828 A1 | 8/2004 | Silverstein et al. |
| 2004/0181239 A1 | 9/2004 | Dorn et al. |
| 2004/0186565 A1 | 9/2004 | Schreck |
| 2004/0186566 A1 | 9/2004 | Hindrichs et al. |
| 2004/0260317 A1 | 12/2004 | Bloom et al. |
| 2004/0260389 A1 | 12/2004 | Case et al. |
| 2005/0004652 A1 | 1/2005 | van der Burg et al. |
| 2005/0004666 A1 | 1/2005 | Alfieri et al. |
| 2005/0075727 A1 | 4/2005 | Wheatley |
| 2005/0080402 A1 | 4/2005 | Santamore et al. |
| 2005/0096498 A1 | 5/2005 | Houser et al. |
| 2005/0107661 A1 | 5/2005 | Lau et al. |
| 2005/0113798 A1 | 5/2005 | Slater et al. |
| 2005/0113810 A1 | 5/2005 | Houser et al. |
| 2005/0113811 A1 | 5/2005 | Houser et al. |
| 2005/0119519 A9 | 6/2005 | Girard et al. |
| 2005/0121206 A1 | 6/2005 | Dolan |
| 2005/0125012 A1 | 6/2005 | Houser et al. |
| 2005/0137688 A1 | 6/2005 | Salahieh et al. |
| 2005/0137695 A1 | 6/2005 | Salahieh et al. |
| 2005/0137698 A1 | 6/2005 | Salahieh et al. |
| 2005/0148815 A1 | 7/2005 | Mortier et al. |
| 2005/0177180 A1 | 8/2005 | Kaganov et al. |
| 2005/0197695 A1 | 9/2005 | Stacchino et al. |
| 2005/0203614 A1 | 9/2005 | Forster et al. |
| 2005/0203615 A1 | 9/2005 | Forster et al. |
| 2005/0203617 A1 | 9/2005 | Forster et al. |
| 2005/0234546 A1 | 10/2005 | Nugent et al. |
| 2005/0240200 A1 | 10/2005 | Bergheim |
| 2005/0251209 A1 | 11/2005 | Saadat et al. |
| 2005/0256567 A1 | 11/2005 | Lim et al. |
| 2005/0288766 A1 | 12/2005 | Plain et al. |

(56) References Cited

U.S. PATENT DOCUMENTS

| | | |
|---|---|---|
| 2006/0004442 A1 | 1/2006 | Spenser et al. |
| 2006/0025784 A1 | 2/2006 | Starksen et al. |
| 2006/0025857 A1 | 2/2006 | Bergheim et al. |
| 2006/0030885 A1 | 2/2006 | Hyde |
| 2006/0042803 A1 | 3/2006 | Gallaher |
| 2006/0047338 A1 | 3/2006 | Jenson et al. |
| 2006/0052868 A1 | 3/2006 | Mortier et al. |
| 2006/0058872 A1 | 3/2006 | Salahieh et al. |
| 2006/0094983 A1 | 5/2006 | Burbank et al. |
| 2006/0129025 A1 | 6/2006 | Levine et al. |
| 2006/0142784 A1 | 6/2006 | Kontos |
| 2006/0161040 A1 | 7/2006 | McCarthy et al. |
| 2006/0161249 A1 | 7/2006 | Realyvasquez et al. |
| 2006/0167541 A1 | 7/2006 | Lattouf |
| 2006/0195134 A1 | 8/2006 | Crittenden |
| 2006/0195183 A1 | 8/2006 | Navia et al. |
| 2006/0229708 A1 | 10/2006 | Powell et al. |
| 2006/0229719 A1 | 10/2006 | Marquez et al. |
| 2006/0241745 A1 | 10/2006 | Solem |
| 2006/0247491 A1 | 11/2006 | Vidlund et al. |
| 2006/0259135 A1 | 11/2006 | Navia et al. |
| 2006/0259136 A1 | 11/2006 | Nguyen et al. |
| 2006/0259137 A1 | 11/2006 | Artof et al. |
| 2006/0276874 A1 | 12/2006 | Wilson et al. |
| 2006/0282161 A1 | 12/2006 | Huynh et al. |
| 2006/0287716 A1 | 12/2006 | Banbury et al. |
| 2006/0287717 A1 | 12/2006 | Rowe et al. |
| 2007/0005131 A1 | 1/2007 | Taylor |
| 2007/0005231 A1 | 1/2007 | Seguchi |
| 2007/0010877 A1 | 1/2007 | Salahieh et al. |
| 2007/0016286 A1 | 1/2007 | Herrmann et al. |
| 2007/0016288 A1 | 1/2007 | Gurskis et al. |
| 2007/0027535 A1 | 2/2007 | Purdy et al. |
| 2007/0038291 A1 | 2/2007 | Case et al. |
| 2007/0050020 A1 | 3/2007 | Spence |
| 2007/0061010 A1 | 3/2007 | Hauser et al. |
| 2007/0066863 A1 | 3/2007 | Rafiee et al. |
| 2007/0073387 A1 | 3/2007 | Forster et al. |
| 2007/0078297 A1 | 4/2007 | Rafiee et al. |
| 2007/0083076 A1 | 4/2007 | Lichtenstein |
| 2007/0083259 A1 | 4/2007 | Bloom et al. |
| 2007/0093890 A1 | 4/2007 | Eliasen et al. |
| 2007/0100439 A1 | 5/2007 | Cangialosi et al. |
| 2007/0112422 A1 | 5/2007 | Dehdashtian |
| 2007/0112425 A1 | 5/2007 | Schaller et al. |
| 2007/0118151 A1 | 5/2007 | Davidson |
| 2007/0118154 A1 | 5/2007 | Crabtree |
| 2007/0118210 A1 | 5/2007 | Pinchuk |
| 2007/0118213 A1 | 5/2007 | Loulmet |
| 2007/0142906 A1 | 6/2007 | Figulla et al. |
| 2007/0161846 A1 | 7/2007 | Nikolic et al. |
| 2007/0162103 A1 | 7/2007 | Case et al. |
| 2007/0168024 A1 | 7/2007 | Khairkhahan |
| 2007/0185565 A1 | 8/2007 | Schwammenthal et al. |
| 2007/0185571 A1 | 8/2007 | Kapadia et al. |
| 2007/0203575 A1 | 8/2007 | Forster et al. |
| 2007/0213813 A1 | 9/2007 | Von Segesser et al. |
| 2007/0215362 A1 | 9/2007 | Rodgers |
| 2007/0221388 A1 | 9/2007 | Johnson |
| 2007/0233239 A1 | 10/2007 | Navia et al. |
| 2007/0239265 A1 | 10/2007 | Birdsall |
| 2007/0256843 A1 | 11/2007 | Pahila |
| 2007/0265658 A1 | 11/2007 | Nelson et al. |
| 2007/0267202 A1 | 11/2007 | Mariller |
| 2007/0270932 A1 | 11/2007 | Headley et al. |
| 2007/0270943 A1 | 11/2007 | Salem et al. |
| 2007/0293944 A1 | 12/2007 | Spenser et al. |
| 2008/0009940 A1 | 1/2008 | Cribier |
| 2008/0065011 A1 | 3/2008 | Marchand et al. |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0082163 A1 | 4/2008 | Woo |
| 2008/0082166 A1 | 4/2008 | Styrc et al. |
| 2008/0091264 A1 | 4/2008 | Machold et al. |
| 2008/0114442 A1 | 5/2008 | Mitchell et al. |
| 2008/0125861 A1 | 5/2008 | Webler et al. |
| 2008/0147179 A1 | 6/2008 | Cai et al. |
| 2008/0154355 A1 | 6/2008 | Benichou et al. |
| 2008/0154356 A1 | 6/2008 | Obermiller et al. |
| 2008/0161911 A1 | 7/2008 | Revuelta et al. |
| 2008/0172035 A1 | 7/2008 | Starksen et al. |
| 2008/0177381 A1 | 7/2008 | Navia et al. |
| 2008/0183203 A1 | 7/2008 | Fitzgerald et al. |
| 2008/0188928 A1 | 8/2008 | Salahieh et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0243150 A1 | 10/2008 | Starksen et al. |
| 2008/0243245 A1 | 10/2008 | Thambar et al. |
| 2008/0255660 A1 | 10/2008 | Guyenot et al. |
| 2008/0255661 A1 | 10/2008 | Straubinger et al. |
| 2008/0281411 A1 | 11/2008 | Berreklouw |
| 2008/0288060 A1 | 11/2008 | Kaye et al. |
| 2008/0293996 A1 | 11/2008 | Evans et al. |
| 2009/0005863 A1 | 1/2009 | Goetz et al. |
| 2009/0048668 A1 | 2/2009 | Wilson et al. |
| 2009/0054968 A1 | 2/2009 | Bonhoeffer et al. |
| 2009/0054974 A1 | 2/2009 | McGuckin, Jr. et al. |
| 2009/0062908 A1 | 3/2009 | Bonhoeffer et al. |
| 2009/0076598 A1 | 3/2009 | Salahieh et al. |
| 2009/0082619 A1 | 3/2009 | De Marchena |
| 2009/0088836 A1 | 4/2009 | Bishop et al. |
| 2009/0099410 A1 | 4/2009 | De Marchena |
| 2009/0112309 A1 | 4/2009 | Jaramillo et al. |
| 2009/0131849 A1 | 5/2009 | Maurer et al. |
| 2009/0132035 A1 | 5/2009 | Roth et al. |
| 2009/0137861 A1 | 5/2009 | Goldberg et al. |
| 2009/0138079 A1 | 5/2009 | Tuval et al. |
| 2009/0157175 A1 | 6/2009 | Benichou |
| 2009/0164005 A1 | 6/2009 | Dove et al. |
| 2009/0171432 A1 | 7/2009 | Von Segesser et al. |
| 2009/0171447 A1 | 7/2009 | Von Segesser et al. |
| 2009/0171456 A1 | 7/2009 | Kveen et al. |
| 2009/0177266 A1 | 7/2009 | Powell et al. |
| 2009/0192601 A1 | 7/2009 | Rafiee et al. |
| 2009/0210052 A1 | 8/2009 | Forster et al. |
| 2009/0216322 A1 | 8/2009 | Le et al. |
| 2009/0222076 A1 | 9/2009 | Figulla et al. |
| 2009/0224529 A1 | 9/2009 | Gill |
| 2009/0234318 A1 | 9/2009 | Loulmet et al. |
| 2009/0234435 A1 | 9/2009 | Johnson et al. |
| 2009/0234443 A1 | 9/2009 | Ottma et al. |
| 2009/0240320 A1 | 9/2009 | Tuval et al. |
| 2009/0248149 A1 | 10/2009 | Gabbay |
| 2009/0276040 A1 | 11/2009 | Rowe et al. |
| 2009/0281619 A1 | 11/2009 | Le et al. |
| 2009/0287299 A1 | 11/2009 | Tabor et al. |
| 2009/0319037 A1 | 12/2009 | Rowe et al. |
| 2009/0326575 A1 | 12/2009 | Galdonik et al. |
| 2010/0016958 A1 | 1/2010 | St. Goar et al. |
| 2010/0021382 A1 | 1/2010 | Dorshow et al. |
| 2010/0023117 A1 | 1/2010 | Yoganathan et al. |
| 2010/0036479 A1 | 2/2010 | Hill et al. |
| 2010/0049313 A1 | 2/2010 | Alon et al. |
| 2010/0082094 A1 | 4/2010 | Quadri et al. |
| 2010/0161041 A1 | 6/2010 | Maisano et al. |
| 2010/0168839 A1 | 7/2010 | Braido et al. |
| 2010/0179641 A1 | 7/2010 | Ryan et al. |
| 2010/0185277 A1 | 7/2010 | Braido et al. |
| 2010/0185278 A1 | 7/2010 | Schankereli |
| 2010/0191326 A1 | 7/2010 | Alkhatib |
| 2010/0192402 A1 | 8/2010 | Yamaguchi et al. |
| 2010/0204781 A1 | 8/2010 | Alkhatib |
| 2010/0210899 A1 | 8/2010 | Schankereli |
| 2010/0217382 A1 | 8/2010 | Chau et al. |
| 2010/0249489 A1 | 9/2010 | Jarvik |
| 2010/0249923 A1 | 9/2010 | Alkhatib et al. |
| 2010/0280604 A1 | 11/2010 | Zipory et al. |
| 2010/0286768 A1 | 11/2010 | Alkhatib |
| 2010/0298755 A1 | 11/2010 | McNamara et al. |

(56) References Cited

U.S. PATENT DOCUMENTS

| | | |
|---|---|---|
| 2010/0298931 A1 | 11/2010 | Quadri et al. |
| 2011/0004296 A1 | 1/2011 | Lutter et al. |
| 2011/0015616 A1 | 1/2011 | Straubinger et al. |
| 2011/0015728 A1 | 1/2011 | Jimenez et al. |
| 2011/0015729 A1 | 1/2011 | Jimenez et al. |
| 2011/0029072 A1 | 2/2011 | Gabbay |
| 2011/0066231 A1 | 3/2011 | Cartledge et al. |
| 2011/0112632 A1 | 5/2011 | Chau et al. |
| 2011/0137397 A1 | 6/2011 | Chau et al. |
| 2011/0137408 A1 | 6/2011 | Bergheim |
| 2011/0224655 A1 | 9/2011 | Asirvatham et al. |
| 2011/0224678 A1 | 9/2011 | Gabbay |
| 2011/0224728 A1 | 9/2011 | Martin et al. |
| 2011/0224784 A1 | 9/2011 | Quinn |
| 2011/0245911 A1 | 10/2011 | Quill et al. |
| 2011/0251682 A1 | 10/2011 | Murray, III et al. |
| 2011/0264206 A1 | 10/2011 | Tabor |
| 2011/0288637 A1 | 11/2011 | De Marchena |
| 2011/0319988 A1 | 12/2011 | Schankereli et al. |
| 2011/0319989 A1 | 12/2011 | Lane et al. |
| 2012/0010694 A1 | 1/2012 | Lutter et al. |
| 2012/0016468 A1 | 1/2012 | Robin et al. |
| 2012/0022640 A1 | 1/2012 | Gross et al. |
| 2012/0035703 A1 | 2/2012 | Lutter et al. |
| 2012/0035713 A1 | 2/2012 | Lutter et al. |
| 2012/0035722 A1 | 2/2012 | Tuval |
| 2012/0059487 A1 | 3/2012 | Cunanan et al. |
| 2012/0089171 A1 | 4/2012 | Hastings et al. |
| 2012/0101571 A1 | 4/2012 | Thambar et al. |
| 2012/0101572 A1 | 4/2012 | Kovalsky et al. |
| 2012/0116351 A1 | 5/2012 | Chomas et al. |
| 2012/0123529 A1 | 5/2012 | Levi et al. |
| 2012/0165930 A1 | 6/2012 | Gifford, III et al. |
| 2012/0179244 A1 | 7/2012 | Schankereli et al. |
| 2012/0203336 A1 | 8/2012 | Annest |
| 2012/0215303 A1 | 8/2012 | Quadri et al. |
| 2012/0283824 A1 | 11/2012 | Lutter et al. |
| 2013/0030522 A1 | 1/2013 | Rowe et al. |
| 2013/0053950 A1 | 2/2013 | Rowe et al. |
| 2013/0059747 A1 | 3/2013 | Mann et al. |
| 2013/0066341 A1 | 3/2013 | Ketai et al. |
| 2013/0079873 A1 | 3/2013 | Migliazza et al. |
| 2013/0131788 A1 | 5/2013 | Quadri et al. |
| 2013/0172978 A1 | 7/2013 | Vidlund et al. |
| 2013/0184811 A1 | 7/2013 | Rowe et al. |
| 2013/0190860 A1 | 7/2013 | Sundt, III |
| 2013/0190861 A1 | 7/2013 | Chau et al. |
| 2013/0197622 A1 | 8/2013 | Mitra et al. |
| 2013/0226288 A1 | 8/2013 | Goldwasser et al. |
| 2013/0231735 A1 | 9/2013 | Deem et al. |
| 2013/0274874 A1 | 10/2013 | Hammer |
| 2013/0282101 A1 | 10/2013 | Eidenschink et al. |
| 2013/0310928 A1 | 11/2013 | Morriss et al. |
| 2013/0317603 A1 | 11/2013 | McLean et al. |
| 2013/0325041 A1 | 12/2013 | Annest et al. |
| 2013/0325110 A1 | 12/2013 | Khalil et al. |
| 2013/0338752 A1 | 12/2013 | Geusen et al. |
| 2014/0081323 A1 | 3/2014 | Hawkins |
| 2014/0094918 A1 | 4/2014 | Vishnubholta et al. |
| 2014/0142691 A1 | 5/2014 | Pouletty |
| 2014/0163668 A1 | 6/2014 | Rafiee |
| 2014/0194981 A1 | 7/2014 | Menk et al. |
| 2014/0214159 A1 | 7/2014 | Vidlund et al. |
| 2014/0222142 A1 | 8/2014 | Kovalsky et al. |
| 2014/0243966 A1 | 8/2014 | Garde et al. |
| 2014/0277419 A1 | 9/2014 | Garde et al. |
| 2014/0296969 A1 | 10/2014 | Tegels et al. |
| 2014/0296970 A1 | 10/2014 | Ekvall et al. |
| 2014/0296971 A1 | 10/2014 | Tegels et al. |
| 2014/0296972 A1 | 10/2014 | Tegels et al. |
| 2014/0296975 A1 | 10/2014 | Tegels et al. |
| 2014/0303718 A1 | 10/2014 | Tegels et al. |
| 2014/0309732 A1 | 10/2014 | Solem |
| 2014/0316516 A1 | 10/2014 | Vidlund et al. |
| 2014/0324160 A1 | 10/2014 | Benichou et al. |
| 2014/0324161 A1 | 10/2014 | Tegels et al. |
| 2014/0324164 A1 | 10/2014 | Gross et al. |
| 2014/0358224 A1 | 12/2014 | Tegels et al. |
| 2014/0364944 A1 | 12/2014 | Lutter et al. |
| 2014/0379076 A1 | 12/2014 | Vidlund et al. |
| 2015/0005874 A1 | 1/2015 | Vidlund et al. |
| 2015/0011821 A1 | 1/2015 | Gorman et al. |
| 2015/0025553 A1 | 1/2015 | Del Nido et al. |
| 2015/0057705 A1 | 2/2015 | Vidlund |
| 2015/0073542 A1 | 3/2015 | Heldman |
| 2015/0073545 A1 | 3/2015 | Braido |
| 2015/0105856 A1 | 4/2015 | Rowe et al. |
| 2015/0119936 A1 | 4/2015 | Gilmore et al. |
| 2015/0119978 A1 | 4/2015 | Tegels et al. |
| 2015/0127096 A1 | 5/2015 | Rowe et al. |
| 2015/0142100 A1 | 5/2015 | Morriss et al. |
| 2015/0142101 A1 | 5/2015 | Coleman et al. |
| 2015/0142103 A1 | 5/2015 | Vidlund |
| 2015/0142104 A1 | 5/2015 | Braido |
| 2015/0173897 A1 | 6/2015 | Raanani et al. |
| 2015/0196393 A1 | 7/2015 | Vidlund et al. |
| 2015/0196688 A1 | 7/2015 | James et al. |
| 2015/0202044 A1 | 7/2015 | Chau et al. |
| 2015/0216653 A1 | 8/2015 | Freudenthal |
| 2015/0216660 A1 | 8/2015 | Pintor et al. |
| 2015/0223820 A1 | 8/2015 | Olson et al. |
| 2015/0223934 A1 | 8/2015 | Vidlund et al. |
| 2015/0238729 A1 | 8/2015 | Jenson et al. |
| 2015/0272731 A1 | 10/2015 | Racchini et al. |
| 2015/0305860 A1 | 10/2015 | Wang et al. |
| 2015/0305864 A1 | 10/2015 | Quadri et al. |
| 2015/0305867 A1 | 10/2015 | Liu et al. |
| 2015/0305868 A1 | 10/2015 | Lutter et al. |
| 2015/0327995 A1 | 11/2015 | Morin et al. |
| 2015/0328001 A1 | 11/2015 | McLean et al. |
| 2015/0335424 A1 | 11/2015 | McLean et al. |
| 2015/0335429 A1 | 11/2015 | Morriss et al. |
| 2015/0342717 A1 | 12/2015 | O'Donnell et al. |
| 2015/0351903 A1 | 12/2015 | Morriss et al. |
| 2015/0351906 A1 | 12/2015 | Hammer et al. |
| 2016/0008131 A1 | 1/2016 | Christianson et al. |
| 2016/0067042 A1 | 3/2016 | Murad et al. |
| 2016/0074160 A1 | 3/2016 | Christianson et al. |
| 2016/0106537 A1 | 4/2016 | Christianson et al. |
| 2016/0113764 A1 | 4/2016 | Sheahan et al. |
| 2016/0143736 A1 | 5/2016 | Vidlund et al. |
| 2016/0151155 A1 | 6/2016 | Lutter et al. |
| 2016/0206280 A1 | 7/2016 | Vidlund et al. |
| 2016/0242902 A1 | 8/2016 | Morriss et al. |
| 2016/0262879 A1 | 9/2016 | Meiri et al. |
| 2016/0262881 A1 | 9/2016 | Schankereli et al. |
| 2016/0317290 A1 | 11/2016 | Chau et al. |
| 2016/0324635 A1 | 11/2016 | Vidlund et al. |
| 2016/0331527 A1 | 11/2016 | Vidlund et al. |
| 2016/0346086 A1 | 12/2016 | Salem |
| 2016/0367365 A1 | 12/2016 | Conklin |
| 2016/0367367 A1 | 12/2016 | Maisano et al. |
| 2016/0367368 A1 | 12/2016 | Vidlund et al. |
| 2017/0079790 A1 | 3/2017 | Vidlund et al. |
| 2017/0128208 A1 | 5/2017 | Christianson et al. |
| 2017/0181854 A1 | 6/2017 | Christianson et al. |
| 2017/0196688 A1 | 7/2017 | Christianson et al. |
| 2017/0252153 A1 | 9/2017 | Chau et al. |
| 2017/0266001 A1 | 9/2017 | Vidlund et al. |

FOREIGN PATENT DOCUMENTS

| | | |
|---|---|---|
| CN | 2902226 Y | 5/2007 |
| CN | 101146484 A | 3/2008 |
| CN | 101180010 A | 5/2008 |
| CN | 101984938 A | 3/2011 |
| CN | 102639179 A | 8/2012 |
| CN | 102869317 A | 1/2013 |
| CN | 102869318 A | 1/2013 |
| CN | 102869321 A | 1/2013 |
| CN | 103220993 A | 7/2013 |
| DE | 2246526 | 3/1973 |
| DE | 19532846 A1 | 3/1997 |
| DE | 19546692 A1 | 6/1997 |

(56) References Cited

FOREIGN PATENT DOCUMENTS

| | | |
|---|---|---|
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049815 A1 | 4/2002 |
| DE | 102006052564 B3 | 12/2007 |
| DE | 102006052710 A1 | 5/2008 |
| DE | 102007043831 A1 | 4/2009 |
| EP | 0103546 A1 | 3/1984 |
| EP | 1057460 A1 | 12/2000 |
| EP | 1088529 A2 | 4/2001 |
| EP | 1469797 B1 | 10/2004 |
| EP | 2111800 A1 | 10/2009 |
| EP | 2193762 A1 | 6/2010 |
| EP | 2278944 A2 | 2/2011 |
| EP | 2747707 A1 | 7/2014 |
| EP | 2918248 A1 | 9/2015 |
| FR | 2788217 A1 | 7/2000 |
| FR | 2815844 A1 | 5/2002 |
| JP | 2003505146 A | 2/2003 |
| JP | 2009514628 A | 4/2009 |
| NL | 1017275 C2 | 8/2002 |
| SU | 1271508 | 11/1986 |
| WO | 9217118 | 10/1992 |
| WO | 9301768 B1 | 2/1993 |
| WO | 9829057 A1 | 7/1998 |
| WO | 9940964 A1 | 8/1999 |
| WO | 9947075 A1 | 9/1999 |
| WO | 0018333 A1 | 4/2000 |
| WO | 0030550 A1 | 6/2000 |
| WO | 200041652 A1 | 7/2000 |
| WO | 200047139 A1 | 8/2000 |
| WO | 01035878 A2 | 5/2001 |
| WO | 2001049213 A2 | 7/2001 |
| WO | 0154625 A1 | 8/2001 |
| WO | 0161289 A1 | 8/2001 |
| WO | 01054624 A1 | 8/2001 |
| WO | 2001056512 A1 | 8/2001 |
| WO | 200176510 A2 | 10/2001 |
| WO | 2001082840 A1 | 11/2001 |
| WO | 0204757 A1 | 1/2002 |
| WO | 2002022054 A1 | 3/2002 |
| WO | 0228321 A2 | 4/2002 |
| WO | 0236048 A1 | 5/2002 |
| WO | 0241789 A1 | 5/2002 |
| WO | 0243620 A1 | 6/2002 |
| WO | 0249540 A2 | 6/2002 |
| WO | 2002076348 A1 | 10/2002 |
| WO | 03003943 A2 | 1/2003 |
| WO | 03030776 A2 | 4/2003 |
| WO | 03049619 A2 | 6/2003 |
| WO | 2003047468 A1 | 6/2003 |
| WO | 2004019825 A1 | 3/2004 |
| WO | 2005102181 A1 | 11/2005 |
| WO | 2006014233 A2 | 2/2006 |
| WO | 2006034008 A2 | 3/2006 |
| WO | 2006070372 A2 | 7/2006 |
| WO | 2006113906 A1 | 10/2006 |
| WO | 2006127756 A2 | 11/2006 |
| WO | 2007081412 A1 | 7/2007 |
| WO | 2008005405 A2 | 1/2008 |
| WO | 2008035337 A2 | 3/2008 |
| WO | 2008091515 A2 | 7/2008 |
| WO | 2008125906 A2 | 10/2008 |
| WO | 2008147964 A1 | 12/2008 |
| WO | 2009024859 A2 | 2/2009 |
| WO | 2009026563 A2 | 2/2009 |
| WO | 2009045338 A1 | 4/2009 |
| WO | 2009132187 A1 | 10/2009 |
| WO | 2010090878 A2 | 8/2010 |
| WO | 2010098857 A1 | 9/2010 |
| WO | 2010121076 A2 | 10/2010 |
| WO | 2011017440 A2 | 2/2011 |
| WO | 2011022658 A1 | 2/2011 |
| WO | 2011069048 A2 | 6/2011 |
| WO | 2011072084 A2 | 6/2011 |
| WO | 2011106735 A1 | 9/2011 |
| WO | 2011109813 A2 | 9/2011 |
| WO | 2011159342 A1 | 12/2011 |
| WO | 2011163275 A2 | 12/2011 |
| WO | 2012027487 A2 | 3/2012 |
| WO | 2012036742 A2 | 3/2012 |
| WO | 2012095116 A1 | 7/2012 |
| WO | 2012177942 A2 | 12/2012 |
| WO | 2013045262 A1 | 4/2013 |
| WO | 2013096411 A1 | 6/2013 |
| WO | 2013175468 A2 | 11/2013 |
| WO | 2014121280 A2 | 8/2014 |
| WO | 2014144937 A2 | 9/2014 |
| WO | 2014162306 A2 | 10/2014 |
| WO | 2014189974 A1 | 11/2014 |
| WO | 2015051430 A1 | 4/2015 |
| WO | 2015058039 A1 | 4/2015 |
| WO | 2015063580 A2 | 5/2015 |
| WO | 2015065646 A1 | 5/2015 |
| WO | 2015120122 A2 | 8/2015 |
| WO | 2015138306 A2 | 9/2015 |
| WO | 2016112085 A2 | 7/2016 |
| WO | 2016126942 A2 | 8/2016 |
| WO | 2016168609 A1 | 10/2016 |
| WO | 2016196933 A1 | 12/2016 |

OTHER PUBLICATIONS

"Shape Memory Alloys," Retrieved from the Internet: <http://webdocs.cs.ualberta.ca/.about.database/MEMS/sma. html>, Feb. 5, 2016, 3 pages.

Al Zaibag, M. et al., "Percutaneous Balloon Valvotomy in Tricuspid Stenosis," British Heart Journal, Jan. 1987, 57 (1):51-53.

Ai-Khaja, N. et al., "Eleven Years' Experience with Carpentier-Edwards Biological Valves in Relation to Survival and Complications," European Journal of Cardiothoracic Surgery, Jun. 30, 1989, 3:305-311.

Almagor, Y. et al., "Balloon Expandable Stent Implantation in Stenotic Right Heart Valved Conduits," Journal of the American College of Cardiology, Nov. 1, 1990, 16(6):1310-1314.

Andersen, H. R. et al., "Transluminal implantation of artificial heart valves. Description of a new expandable aortic valve and initial results with implantation by catheter technique in closed chest pigs," European Heart Journal, 1992, 13(5):704-708.

Andersen, H. R. "History of Percutaneous Aortic Valve Prosthesis," Herz, Aug. 2009, 34(5):343-346.

Andersen, H. R., "Transluminal catheter implanted prosthetic heart valves," International Journal of Angiology, 1998, 7(2):102-106.

Ashton, R. C., Jr. et al., "Development of an Intraluminal Device for the Treatment of Aortic Regurgitation: Prototype and in Vitro Testing System," Journal of Thoracic and Cardiovascular Surgery, 1996, 112:979-983.

Benchimol, A. et al., "Simultaneous Left Ventricular Echocardiography and Aortic Blood Velocity During Rapid Right Ventricular Pacing in Man," The American Journal of the Medical Sciences, Jan.-Feb. 1977, 273(1):55-62.

Bemacca G. M. et al. "Polyurethane heart valves: Fatigue failure, calcification, and polyurethane structure," Journal of Biomedical Materials Research, Mar. 5, 1997, 34(3):371-379.

Boudjemline, Y. et al., "Steps Toward the Percutaneous Replacement of Atrioventricular Valves: An Experimental Study," Journal of the American College of Cardiology, Jul. 2005, 46(2):360-365.

Buckberg, G. et al., "Restoring Papillary Muscle Dimensions During Restoration in Dilated Hearts," Interactive Cardiovascular and Thoracic Surgery, 2005, 4:475-477.

Chamberlain, G., "Ceramics Replace Body Parts," Design News, Jun. 9, 1997, Issue 11, vol. 52, 5 pages.

Choo, S. J. et al., "Aortic Root Geometry: Pattern of Differences Between Leaflets and Sinuses of Valsava," The Journal of Heart Valve Disease, Jul. 1999, 8:407-415.

Declaration of Malcolm J. R. Dalrymple-Hay, Nov. 9, 2012, pp. 1-11; with Curriculum Vitae, Oct. 4, 2012.

(56) References Cited

OTHER PUBLICATIONS

Dotter, C. T. et al., "Transluminal Treatment of Arteriosclerotic Obstruction. Description of a New Technic and a Preliminary Report of its Application," Circulation, Nov. 1964, 30:654-670.
Drawbaugh, K., "Feature—Heart Surgeons Explore Minimally Invasive Methods," Reuters Limited, Jul. 16, 1996, 3 pages.
Gray, H., The Aorta, Anatomy of the Human Body, 1918, Retrieved from the Internet <http://www.bartleby. com/107/142.html>, Dec. 10, 2012, 5 pages.
Gray, H., The Heart, Anatomy of the Human Body, 1918, Retrieved from the Internet <http://education.yahoo.com/reference/gray/subjects/subject/1- 38>, Aug. 10, 2012, 9 pages.
Greenhalgh, E. S., "Design and characterization of a biomimetic prosthetic aortic heart valve," 1994, ProQuest Dissertations and Theses, Department of Fiber and Polymer Science, North Carolina State University at Raleigh, 159 pages. cited byapplicant.
Inoue, K. et al., "Clinical Application of Transvenous Mitral Commissurotomy by a New Balloon Catheter," The Journal of Thoracic and Cardiovascular Surgery, 1984, 87:394-402.
Jin, X. Y. et al., "Aortic Root Geometry and Stentless Porcine Valve Competence," Seminars in Thoracic and Cardiovascular Surgery, Oct. 1999, 11(4):145-150.
Knudsen, L. L. et al., "Catheter-implanted prosthetic heart valves. Transluminal catheter implantation of a new expandable artificial heart valve in the descending thoracic aorta in isolated vessels and closed chest pigs," The International Journal of Artificial Organs, 1993, 16(5):253-262.
Kolata, G., "Device That Opens Clogged Arteries Gets a Failing Grade in a New Study," New York Times [online], <http://www.nytimes.com/1991/01/03/health/device-that-opens-clogged-ar- teries-gets-a-faili . . . ,>, published Jan. 3, 1991,retrieved from the Internet on Feb. 5, 2016, 3 pages.
Lawrence, D. D., "Percutaneous Endovascular Graft: Experimental Evaluation," Radiology, 1987, 163:357- 360.
Lozonschi, L., et al. "Transapical mitral valved stent implantation: A survival series in swine," The Journal of Thoracic and Cardio- vascular Surgery, 140(2):422-426 (Aug. 2010) published online Mar. 12, 2010, 1 page.
Lutter, G. et al., "Mitral Valved Stent Implantation," European Journal of Cardio-Thoracic Surgery, 2010, 38:350-355, 2 pages.
Ma, L. et al., "Double-crowned valved stents for off-pump mitral valve replacement," European Journal of Cardio-Thoracic Surgery, Aug. 2005, 28(2): 194-198.
Moazami, N. et al., "Transluminal aortic valve placement: A feasibility study with a newly designed collapsible aortic valve," ASAIO Journal, Sep./Oct. 1996, 42(5):M381-M385.
Orton, C., "Mitralseal: Hybrid Transcatheter Mitral Valve Replacement," Retrieved from the Internet: <http:/www.acvs.org/symposium/proceedings2011/data/papers/102.pdf>, pp. 311-312.

Pavcni K, D. et al. "Development and Initial Experimental Evaluation of a Prosthetic Aortic Valve for Transcatheter Placement," Radiology, 1992; 183:151-154.
Porstmann, W. et al., "Der Verschlu.beta. des Ductus Arteriosus Persistens ohne Thorakotomie," Thoraxchirurgie Vaskulare Chirurgie, Band 15, Heft 2, Stuttgart, Apr. 1967, pp. 199-203.
Rashkind, W. J., "Creation of an Atrial Septal Defect Without Thoracotomy," The Journal of the American Medical Association, Jun. 13, 1966, 196(11):173-174.
Rashkind, W. J., "Historical Aspects of Interventional Cardiology: Past, Present, Future," Texas Heart Institute Journal, Dec. 1986, 13(4):363-367.
Reul, H. et al., "The Geometry of the Aortic Root in Health, at Valve Disease and After Valve Replacement," J. Biomechanics, 1990, 23(2):181-191.
Rosch, J. et al., "The Birth, Early Years and Future of Interventional Radiology," J Vasc Interv Radiol., Jul. 2003, 4:841-853.
Ross, D. N., "Aortic Valve Surgery," Guys Hospital, London, 1968, pp. 192-197.
Rousseau, E. P. M. et al., "A mechanical analysis of the closed Hancock heart valve prosthesis," Journal of Biomechanics, 1988, 21(7):545-562.
Sabbah, A. N. et al., "Mechanical Factors in the Degeneration of Porcine Bioprosthetic Valves: An Overview," Dec. 1989, Journal of Cardiac Surgery, 4(4):302-309.
Selby, J. B., "Experience with New Retrieval Forceps for Foreign Body Removal in the Vascular, Urinary, and Biliary Systems," Radiology, 1990, 176:535-538.
Serruys, P. W. et al., "Stenting of Coronary Arteries. Are we the Sorcerer's Apprentice?," European Heart Journal , Sep. 1989, 10(9):774-782.
Sigwart, U., "An Overview of Intravascular Stents: Old and New," Chapter 48, Interventional Cardiology, 2nd Edition, W.B. Saunders Company, Philadelphia, PA, COPYRGT. 1994, 1990, pp. 803-815.
Tofeig, M. et al., "Transcatheter Closure of a Mid-Muscular Ventricular Septal Defect with an Amplatzer VSD Occluder Device," Heart, 1999, 81:438-440.
Uchida, B. T. et al., "Modifications of Gianturco Expandable Wire Stents," Am. J. Roentgenol., May 1988, 150 (5):1185-1187.
US 9,155,620, Oct. 2015, Gross et al. (withdrawn).
Watt, A. H. et al., "Intravenous Adenosine in the Treatment of the Supraventricular Tachycardia; a Dose-Ranging Study and Interaction with Dipyridamole," British Journal of Clinical Pharmacology, 1986, 21:227-230.
Webb, J. G. et al., "Percutaneous Aortic Valve Implantation Retrograde from the Femoral Artery," Circulation, 2006, 113:842-850.
Wheatley, D. J., "Valve Prostheses," Rob & Smith's Operative Surgery, Fourth Edition, 1986, pp. 415-424, Butterworths.
Yoganathan, A. P. et al., "The Current Status of Prosthetic Heart Valves," In Polymetric Materials and Artificial Organs, American Chemical Society, 1984, pp. 111-150.

\* cited by examiner

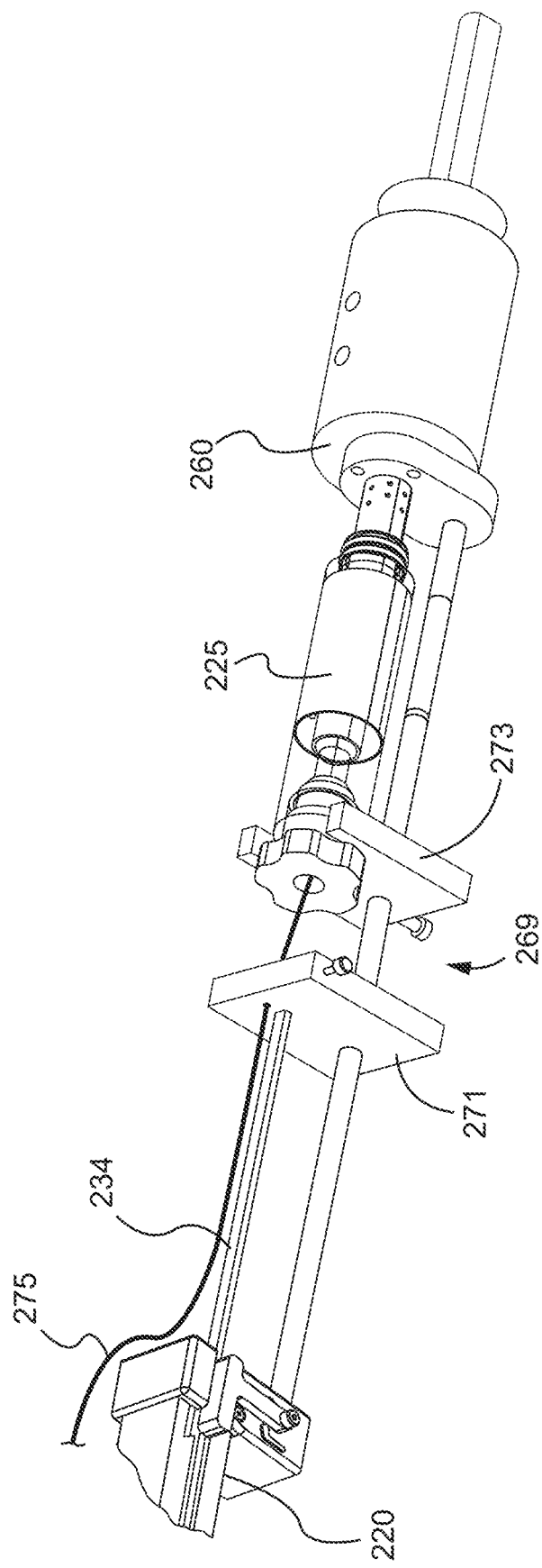

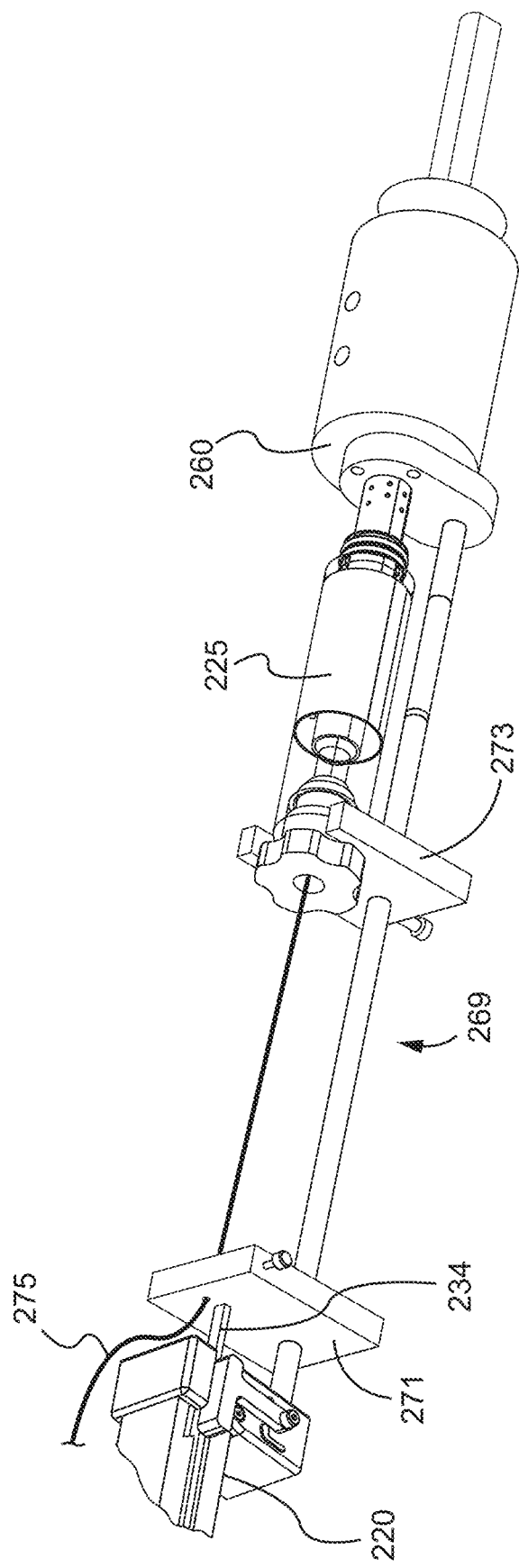

APPARATUS AND METHODS FOR DELIVERY OF TRANSCATHETER PROSTHETIC VALVES

CROSS-REFERENCE TO RELATED APPLICATIONS

This application is a continuation of U.S. patent application Ser. No. 15/388,571, filed Dec. 22, 2016, which is a continuation of U.S. Pat. No. 9,526,611, filed Oct. 29, 2014, which claims priority to and the benefit of U.S. Provisional Patent Application No. 61/896,664, filed Oct. 29, 2013, entitled "Improved Delivery Systems for Transcatheter Prosthetic Valves," each of the disclosures of which is incorporated herein by reference in its entirety.

BACKGROUND

Embodiments are described herein that relate to devices and methods for use in the delivery and deployment of transcatheter prosthetic valves, and particularly to devices and methods for delivering expandable prosthetic heart valves.

Prosthetic heart valves can pose particular challenges for delivery and deployment within a heart. Valvular heart disease, and specifically, aortic and mitral valve disease is a significant health issue in the United States (US); annually approximately 90,000 valve replacements are conducted in the US. Traditional valve replacement surgery involving the orthotopic replacement of a heart valve, is considered an "open heart" surgical procedure. Briefly, the procedure necessitates surgical opening of the thorax, the initiation of extra-corporeal circulation with a heart-lung machine, stopping and opening of the heart, excision and replacement of the diseased valve, and re-starting of the heart. While valve replacement surgery typically carries a 1-4% mortality risk in otherwise healthy persons, a significantly higher morbidity is associated to the procedure largely due to the necessity for extra-corporeal circulation. Further, open heart surgery is often poorly tolerated in elderly patients. Thus elimination of the extra-corporeal component of the procedure could result in reduction in morbidities and cost of valve replacement therapies could be significantly reduced.

While replacement of the aortic valve in a transcatheter manner is the subject of intense investigation, lesser attention has been focused on the mitral valve. This is in part reflective of the greater level of complexity associated to the native mitral valve apparatus, and thus, a greater level of difficulty with regards to inserting and anchoring the replacement prosthesis. A need exists for delivery devices and methods for transcatheter mitral valve replacements.

SUMMARY

Apparatus and methods are described herein for use in the delivery of a transcatheter prosthetic mitral valve replacement. In some embodiments, an apparatus includes a catheter assembly including a sheath, a hub and a traveler strap, and a handle assembly including an actuator and an elongate shaft. The handle assembly can be removably coupled to the catheter assembly. A valve holding tube defines a lumen configured to receive a prosthetic mitral valve in a compressed configuration and is configured to be removably coupled to a distal end portion of the elongate shaft of the handle assembly. A distal end portion of the valve holding tube can be received within an interior region of the hub when the valve holding tube is coupled to the elongate shaft of the handle assembly. The actuator when actuated is configured to cause the tensioning unit to travel along the traveler strap moving the handle assembly distally such that a distal end of the elongate shaft moves the prosthetic mitral valve distally out of the valve holding tube and out a distal end of the sheath such that the prosthetic mitral valve is free to move to a biased expanded configuration.

BRIEF DESCRIPTION OF THE FIGURES

FIG. 15 is a side perspective view of a portion of the handle assembly of FIG. 4 coupled to a load assist device according to an embodiment with the load assist device in a first position.

FIG. 16 is a side perspective view of the portion of the handle assembly and load assist device of FIG. 15 with the load assist device in a second position.

DETAILED DESCRIPTION

Figure 1:
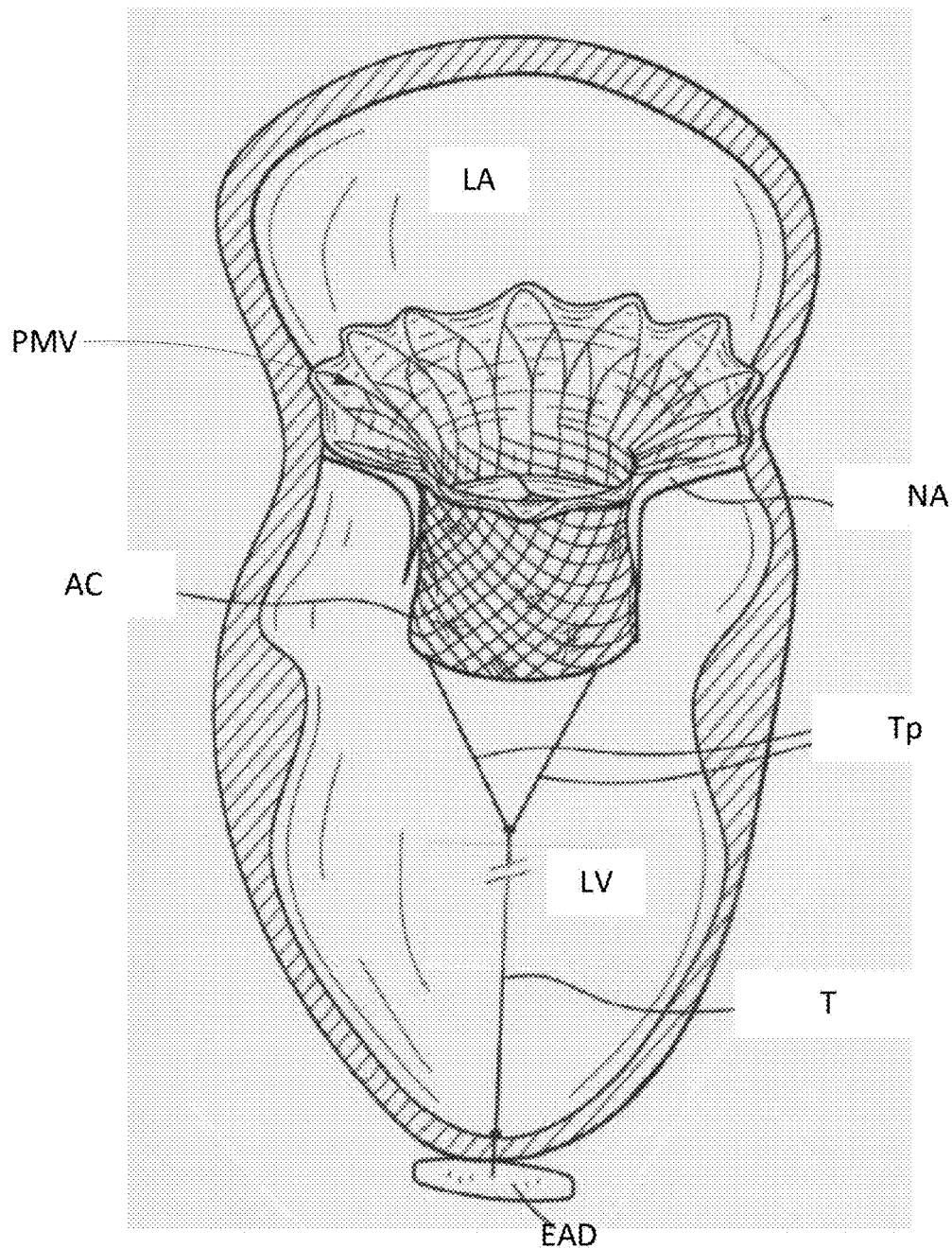
FIG. 1 is a cross-sectional illustration of portion of a heart with a prosthetic mitral valve implanted therein.

Apparatus and methods are described herein for use in the delivery and deployment of a prosthetic mitral valve into a heart. As described herein, in some embodiments, a delivery device can include a handle assembly having an actuator, a delivery catheter and a valve holding tube. The valve holding tube can be removably coupled to a distal end portion of an elongate sheath of the handle assembly and the valve holding tube and handle assembly can be collectively and movably coupled to the delivery catheter. A dilator device is also described herein that can optionally be used during a procedure to deliver a prosthetic mitral valve to the heart and can be received through a lumen of the delivery catheter and used prior to inserting the handle assembly and holding tube into the delivery catheter. The delivery device described herein can be used to deploy a prosthetic mitral valve into the heart in a controlled manner providing incremental movement of the prosthetic mitral valve within the delivery catheter and out into the heart.

In some embodiments, a method of delivering a transcatheter mitral valve replacement to the mitral annulus of a heart includes deploying into the mitral annulus a transcatheter mitral valve prosthesis using a delivery device as described herein. The transcatheter mitral valve prosthesis can be made from an expandable metal stent body having valve leaflets disposed therein. The stent body can be covered with a synthetic material or stabilized pericardial tissue and the valve leaflets can be made from stabilized pericardial tissue. The expandable metal stent body can have an optional atrial cuff and the cuff can optionally have a covering made from a synthetic material and/or stabilized pericardial tissue. The transcatheter mitral valve prosthesis can be deployed via catheter in a compressed state and expanded upon ejection from the catheter. The mitral valve prosthesis may include one or more tethers coupled to a proximal end of the prosthesis.

A distal end of the one or more tethers can be anchored in the left ventricle. The one or more tethers can be tightened by a catheter tool positioned in the left atrium that can pull the proximal end of the one or more tethers just prior to fastening the one or more tethers to establish a fixed length. Prosthetic mitral valves that can be delivered with the devices and methods disclosed herein can include those disclosed in International Patent Application Serial Nos. PCT/US14/40188 entitled "Structural Members for Prosthetic Mitral Valves," filed May 30, 2014 ("PCT application '40188"), PCT/US14/44047 entitled "Thrombus Management and Structural Compliance Features For Prosthetic Heart Valves," filed Jun. 25, 2014 ("PCT application '44047"), and PCT/US14/58826 entitled "Prosthetic Heart Valve and Systems and Methods for Delivering the Same," filed Oct. 2, 2014 ("PCT application '58826"), the disclosures of which are incorporated herein by reference.

In some embodiments, a surgical kit can include a delivery device as described herein and accessory components that can be used with the delivery device in a procedure to deliver a transcatheter prosthetic valve as described herein. The delivery device and the accessory components can be disposed within a sterile package. For example, in some embodiments, a kit can include a delivery device and a dilator device and/or a valve loading device as described herein. In some embodiments, a kit can also include a transcatheter valve (e.g., a prosthetic mitral valve) and/or an epicardial pad that can be used to secure the transcatheter valve in position within the heart.

As used herein, the words "proximal" and "distal" refer to a direction closer to and away from, respectively, an operator of, for example, a medical device. Thus, for example, the end of the medical device closest to the patient's body (e.g., contacting the patient's body or disposed within the patient's body) would be the distal end of the medical device, while the end opposite the distal end and closest to, for example, the user (or hand of the user) of the medical device, would be the proximal end of the medical device.

FIG. 1 is a cross-sectional illustration of the left ventricle LV and left atrium LA of a heart having a transcatheter prosthetic mitral valve PMV deployed therein and an epicardial anchor device EAD securing the prosthetic mitral valve PMV in place. FIG. 1 illustrates the prosthetic mitral valve PMV seated into the native valve annulus NA and held there using an atrial cuff AC of the prosthetic mitral valve PMV, the radial tension from the native leaflets, and a ventricular tether T secured with attachment portions Tp to the prosthetic mitral valve PMV and to the epicardial anchor EAD. The apparatus and methods described herein can be used in conjunction with the various different types and embodiments of an epicardial anchor device, such as those described in pending International Patent Application No. PCT/2014/049218 entitled "Epicardial Anchor Devices and Methods," ("PCT application '049218") the disclosure of which is incorporated herein by reference in its entirety.

Figure 2:
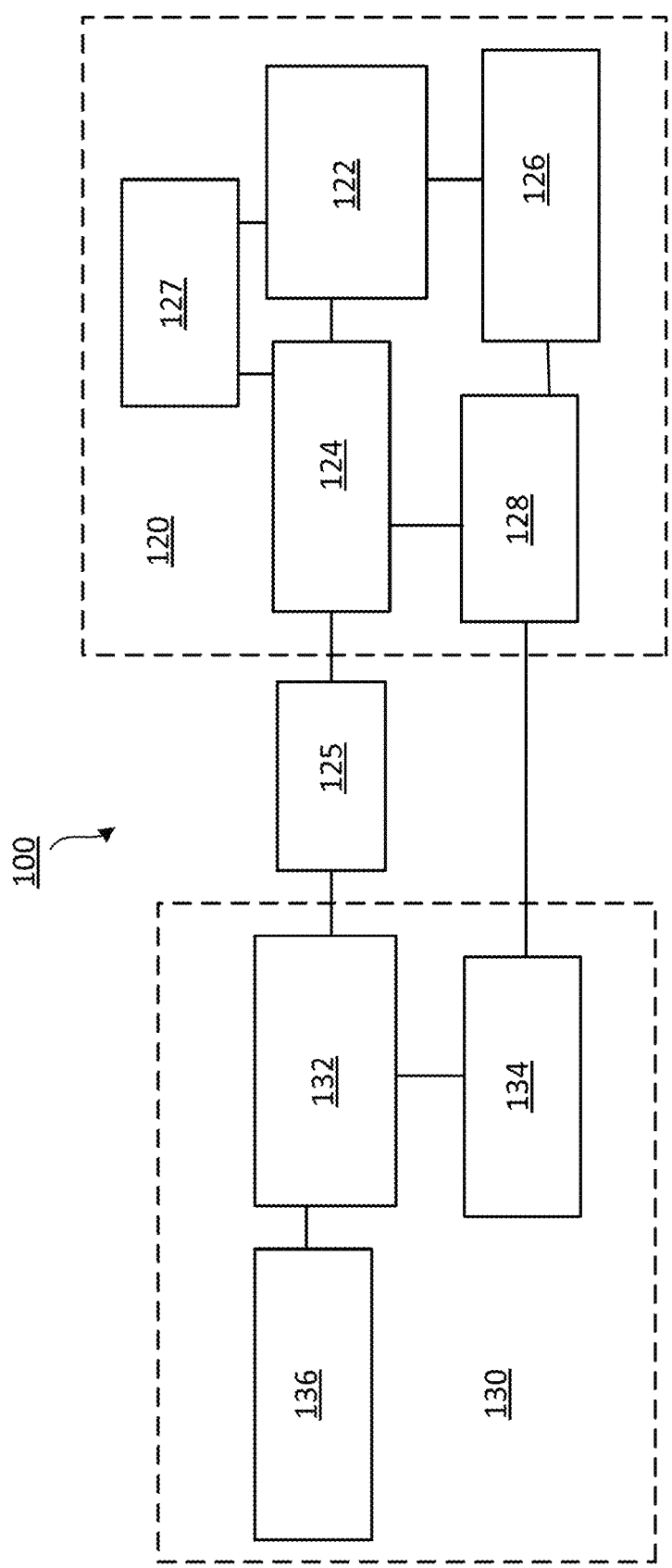
FIG. 2 is a schematic illustration of a delivery device, according to an embodiment.

FIG. 2 is a schematic illustration of a delivery device, according to an embodiment. A delivery device 100 can be used to deliver and deploy a prosthetic heart valve within the heart, such as, for example, a prosthetic mitral valve. The delivery device 100 includes a catheter assembly 130, a handle assembly 120 removably coupleable to the catheter assembly 130, and a valve holding tube 125 removably couplable to the handle assembly 120.

The catheter assembly 130 includes a hub 132, a delivery sheath 136 and a traveler strap 134. The delivery sheath 136 defines a lumen (not shown in FIG. 2) through which the valve holding tube 125 can be inserted to deliver a prosthetic valve (not shown in FIG. 2) disposed within the valve holding tube 125 as described in more detail below. The hub 132 is disposed at a proximal end of the sheath 136 and defines an interior region through which the prosthetic valve is first introduced prior to insertion into the lumen of the sheath 136. In use, the hub 132 remains outside the heart and can provide access to the lumen of the sheath when it is inserted into the heart. The traveler strap 134 is coupled to the hub 132 and extends proximally from the hub 132. The traveler strap 134 is a thin or narrow elongate strap that can engage the handle assembly 120 as described in more detail below. The traveler strap 134 can be formed with, for example, various plastic and metal materials suitable for medical use.

The handle assembly includes a housing 122, an actuator 126 coupled to the housing 122, a tensioning unit 128 coupled to the housing 122, an elongate shaft 124 coupled to the housing 122 and extending distally from the housing 122, and a positioner 127 coupled to the housing 122. The actuator 126 can be in the form of a grip that is pivotally coupled to the housing 122 and a spring can bias the actuator 126 away from the housing 122. The actuator 126 is operatively coupled to the tensioning unit 128 such that when the actuator 126 is actuated by the user (e.g., gripped or squeezed such that a force is exerted against the spring), the actuator 126 causes the tensioning unit 128 to move a strap mount (not shown in FIG. 2) of the tensioning unit 128. The traveler strap 134 of the catheter assembly 130 can be coupled to the handle assembly 120 such that the traveler strap 134 engages the strap mount of the tensioning unit 128. Actuation of the tensioning unit 128 pulls the handle assembly 120 distally along the traveler strap 134. In some embodiments, the traveler strap 134 engages the strap mount with a friction fit. In some embodiments, the traveler strap 134 includes teeth along at least a portion of a length of the traveler strap 134 that engage the strap mount. Thus, the tensioning unit 128 can include a pawl coupled to the actuator such that the tensioning unit can function as a ratcheting mechanism to draw the handle assembly 120 along the traveler strap 134 with each actuation of the actuator 126.

The valve holding tube 125 can contain or hold a prosthetic mitral valve (not shown in FIG. 2) in a compressed configuration within an interior lumen of the valve holding tube 125. Although not shown in FIG. 2, in some embodiments, a valve loading device can be used to load the prosthetic valve into the valve holding tube 125 such that the prosthetic valve is compressed in a controlled manner to a desired compressed size and shape. Such a valve loading device is described in more detail below with reference to a specific embodiment. The valve holding tube 125 (with the prosthetic mitral valve therein) can be coupled to a distal end portion of the elongate shaft 124 of the handle assembly 120. For example, a portion of the distal end portion of the elongate shaft 124 of the handle assembly 120 can be received within an interior region of the valve holding tube 125. Prior to coupling the valve holding tube 125 to the elongate shaft 124, a tether (not shown) coupled to the prosthetic valve (within the valve holding tube 125) can be threaded through a lumen defined by the elongate shaft 124 and extend proximally out of the handle assembly 120.

The valve holding tube 125 can have various lengths to accommodate various different procedures to deliver the prosthetic heart valve to the heart. For example, in some embodiments, the valve holding tube 125 can have a length of between about 10 cm and 150 cm. In some embodiments, the valve holding tube 125 can have a length of about 12 cm to about 38 cm. In some embodiments, the valve holding tube 125 can have a length of about 50 cm to about 150 cm.

In some embodiments, the prosthetic heart valve (e.g., mitral valve) can be delivered apically, i.e. delivered through the apex of the left ventricle of the heart, using the delivery device 100 described herein. With such apical delivery, the delivery device 100 can access the heart and pericardial space by intercostal delivery. In this case, the valve holding tube 125 can have a length of, for example, 12-38 cm.

In another delivery approach, the delivery device 100 can deliver the prosthetic heart valve using either an antegrade or retrograde delivery approach without requiring the use of a rigid tube system that is commonly used in such procedures. In another embodiment, the delivery device 100 can access the heart via a trans-septal approach. In either case, where a long distance must be travelled, the valve holding tube 125 can have a length of, for example, 60-150 cm.

The positioner 127 can be mounted to a proximal end portion of the housing 122. A thumb screw or set screw can be used to secure the positioner to the housing 122. One or more tethers coupled to the prosthetic valve can extend through the handle assembly 120 and can also be inserted or threaded through the positioner 127. The positioner 127 can be used to fine tune the advancement or deployment of the mitral valve within the catheter assembly 130 and into the heart. A vise mechanism can be tightened around the tether to lock it in place. The positioner 127 can include a wheel or dial that can be rotated to adjust the tension on the tether to thereby adjust the speed at which the prosthetic valve can be deployed. When the dial is turned, a center tube extends proximally out of the positioner 127. The center tube includes deployment distance markings that can be used to inform the user how far the prosthetic valve has been advanced during the deployment procedure. The markings can be, for example, labeled with numbers or letters, or can be color coded. To deploy the prosthetic valve, the dial is rotated counterclockwise and to reposition the valve the dial is rotated clockwise. For example, after initially deploying the prosthetic valve, it may be desirable to repositioning the valve by retracting the valve into the sheath 136 of the catheter assembly 130. The tether attached to the prosthetic valve can be tightened, for example, using a slight rotation clockwise.

The positioner 127 can provide additional safety during a deployment procedure in that, with a compressed valve under great pressure, release from a catheter can launch the prosthetic valve, for example, a distance of many feet. However, with the positioner 127 provided herein and the ability to provide a slow calibrated deployment, the user can control the deployment to prevent the valve from inadvertently being projected from the valve holding tube 125 and sheath 136.

In use to deliver and deploy the prosthetic mitral valve within a heart, the sheath 136 of the catheter assembly 130 can be inserted through the epicardial surface of the patient's heart and extended through the left ventricle and to the left atrium of the heart such that the hub 132 is disposed on the outside of the heart near or in contact with the epicardial surface. In some embodiments, prior to introducing the sheath 136 into the heart, a guidewire is extended into the heart and to the left atrium. The sheath 136 can then be threaded over the guidewire to be inserted into the heart. In some embodiments, prior to inserting the sheath 136 into the heart, a dilator device (not shown in FIG. 2) can be inserted through the hub 132 and through the lumen of the sheath 136, such that a tapered distal end portion of the dilator device extends outside a distal end of the sheath 136. The tapered distal end of the dilator device can provide a lead-in for the sheath 136 and help open or enlarge the entry opening at the epicardial surface and through the mitral annulus. When the sheath 136 is placed at the desired position within the heart, the dilator device can be removed leaving the sheath 136 within the heart.

With the valve holding tube 125 coupled to the distal end portion of the elongate shaft 124 of the handle assembly 120, the traveler strap 134 of the catheter assembly 130 can be coupled to the strap mount of the tensioning unit 128 of the handle assembly 120. The valve holding tube 125 can then be inserted into the hub 132 of the catheter assembly 130 and o-rings (not shown in FIG. 1) on the valve holding tube 125 can maintain the position of the valve holding tube 125 within the hub 132. The actuator 126 of the handle assembly 120 can then be actuated by squeezing the actuator grip toward the housing 122 of the handle assembly 120 to cause the tensioning unit 128 to move or pull the handle assembly 120 distally along the traveler strap 134. As the handle assembly 120 moves distally, a distal end of the shaft 124 of the handle assembly 120 pushes the prosthetic valve out of the valve holding tube 125, into the lumen of the sheath 136 of the catheter assembly 130 and eventually out a distal end of the sheath 136 and into the left atrium of the heart. As the handle assembly 120 moves distally, the valve loading tube 125 remains stationary allowing the elongate shaft 124 of the handle assembly 120 to push the prosthetic valve out of the valve holding tube 125. After the prosthetic valve has been deployed, the positioner 127 can be used to help reposition the valve as needed.

FIGS. 3-9 illustrate a delivery device according to one implementation of the delivery device illustrated schematically in FIG. 2. A delivery device 200 includes a catheter assembly 230, a handle assembly 220 removably couplable to the catheter assembly 230 and a valve holding tube 225 removably couplable to the handle assembly 220. The delivery device 200 can be used to deliver and deploy a prosthetic heart valve within the heart, such as, for example, a prosthetic mitral valve (not shown) as described above for the previous embodiment.

The catheter assembly 230 includes a hub 232, a delivery sheath 236 and a traveler strap 234. The delivery sheath 236 defines a lumen 237 (see FIG. 7) through which a prosthetic valve can moved distally to deliver to a heart as described in more detail below. The hub 232 is disposed at a proximal end of the sheath 236 and defines an interior region 238 through which the valve holding tube 225 in which a prosthetic valve is disposed can be inserted. The traveler strap 234 is coupled to the hub 232 and extends proximally from the hub 232 as shown, for example, in FIGS. 3 and 7. The traveler strap 234 can be formed the same as or similar to the traveler strap 134 described above and can be coupled to the handle assembly 220 as described in more detail below.

Figure 5:
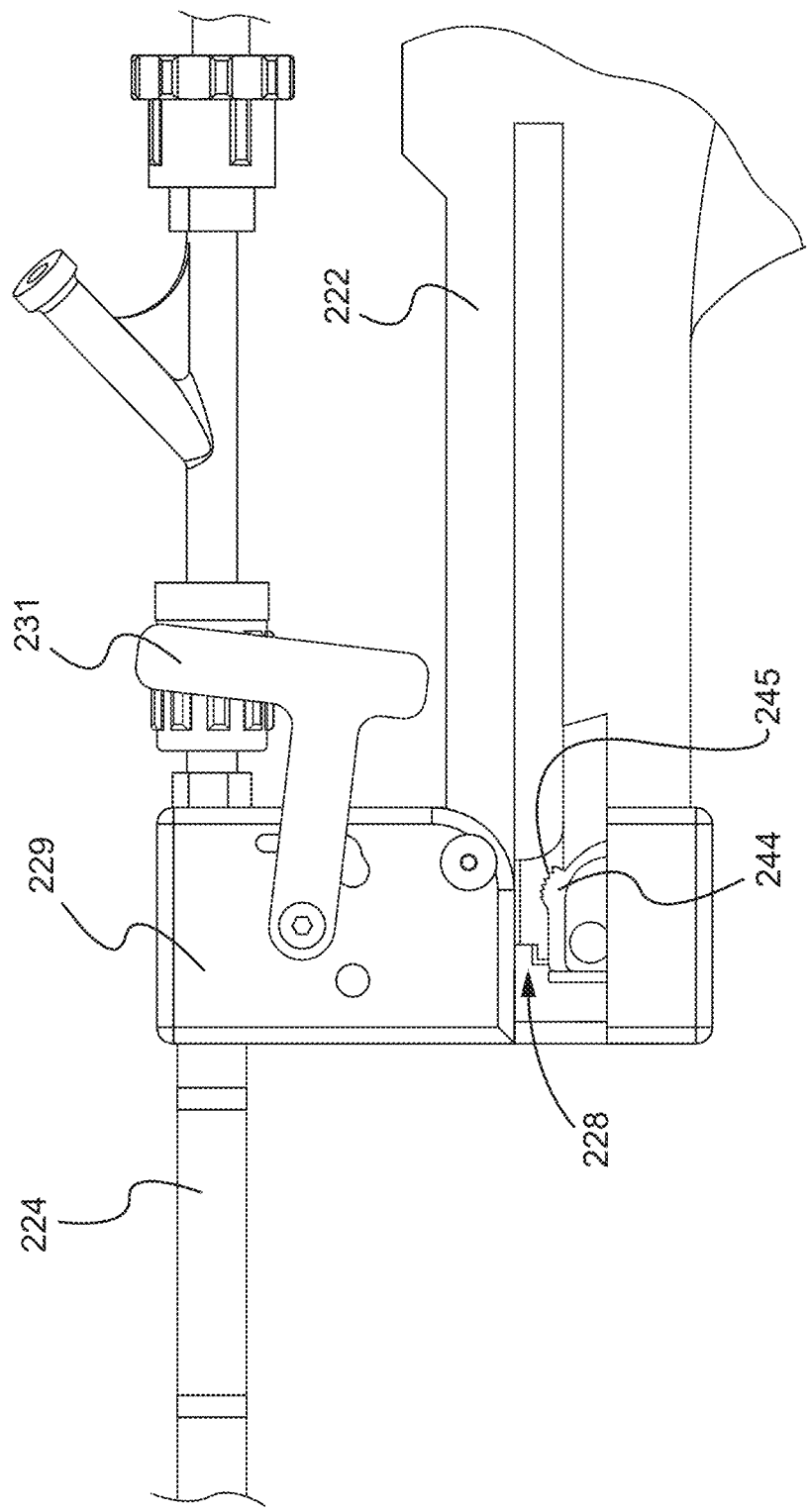
FIG. 5 is an enlarged side view of a portion the handle assembly of FIG. 4.
Figure 6:
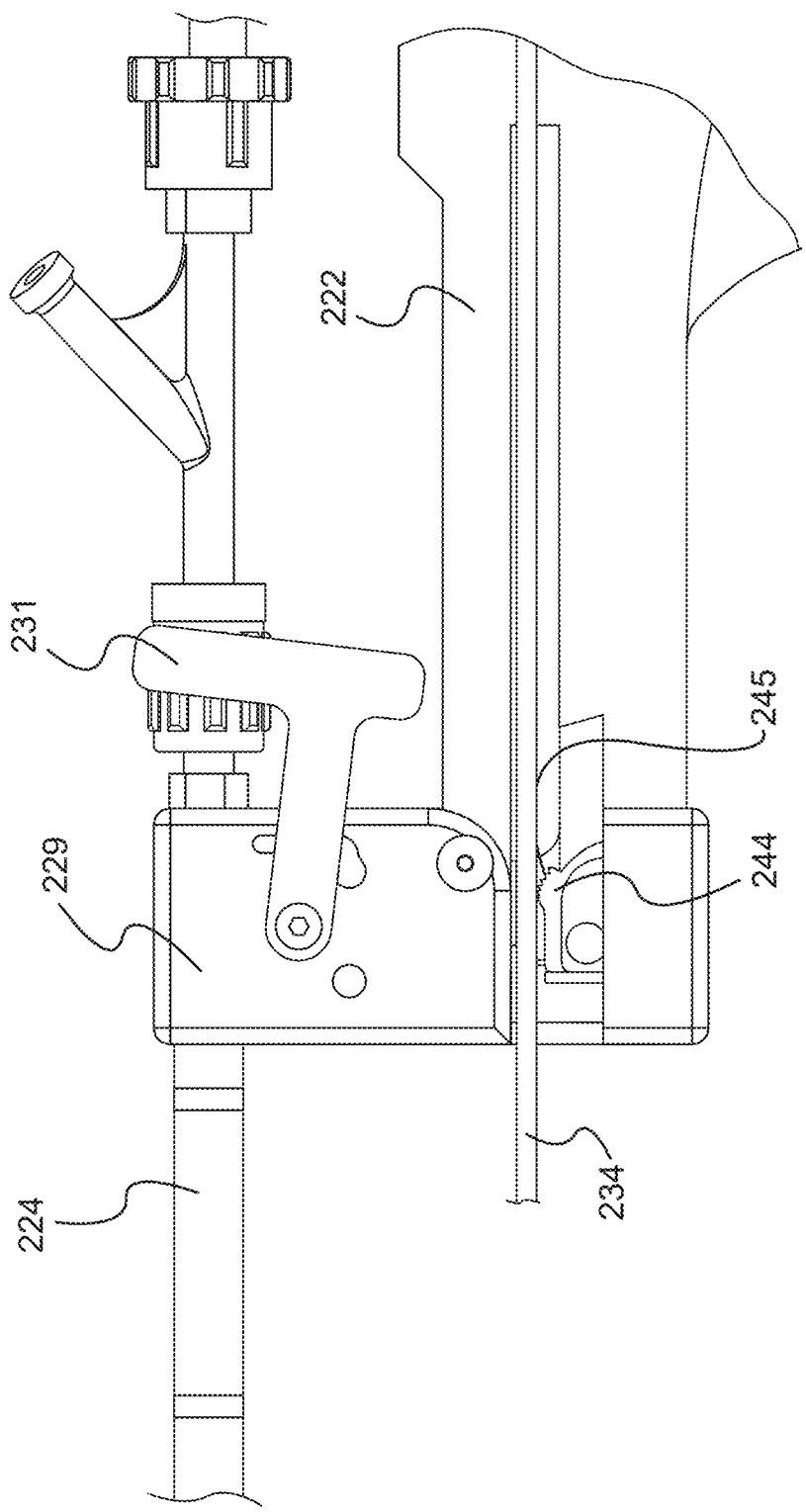
FIG. 6 is an enlarged side view of a portion the handle assembly of FIG. 4 shown with a portion of traveler strap coupled thereto.
Figure 7:
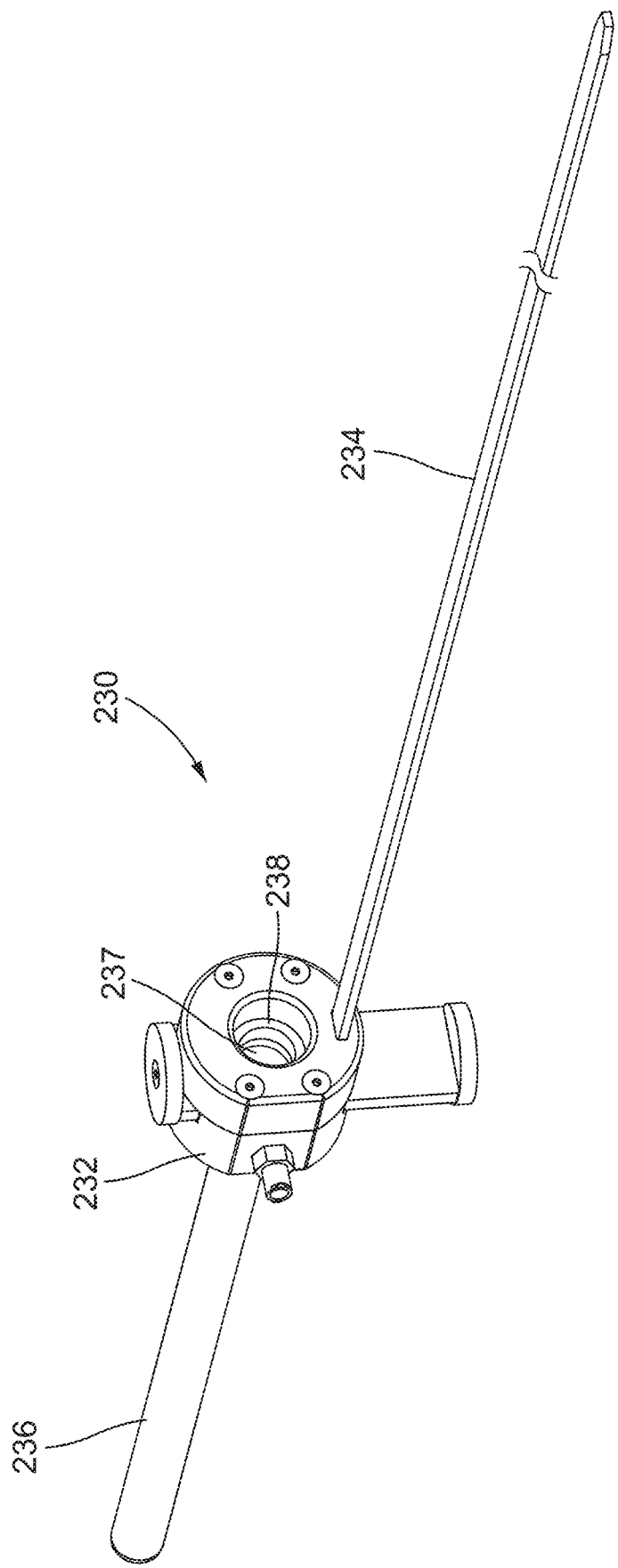
FIG. 7 is a perspective view of a catheter assembly of the delivery device of FIG. 3.
Figure 8:
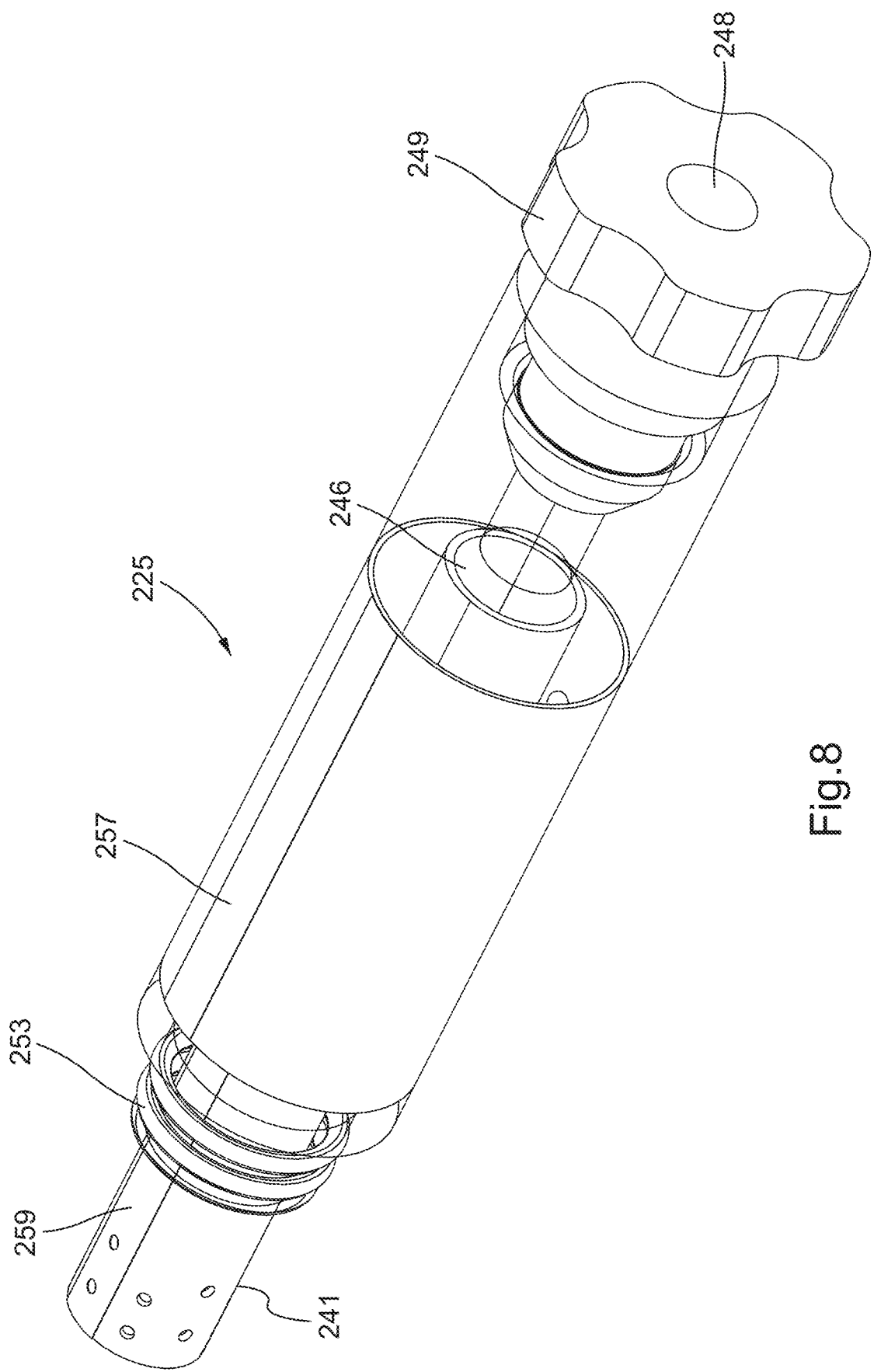
FIG. 8 is a perspective view of a valve holding tube of the delivery device of FIG. 3.

The handle assembly 220 includes a housing 222, an actuator 226, a tensioning unit 228 (see FIGS. 5 and 6), an elongate shaft 224 and a positioner 227. The handle assembly 220 also includes a coupling block 229 that is used to couple the elongate shaft 224 to the housing 222. A hemostasis Y-adapter 239 disposed between the positioner 227 and the coupling block 229. The Y-adapter 239 can be used to connect, for example, a fluid line to the delivery device 200 to, for example, flush and purge the interior of the elongate shaft 224. The actuator 226 is in the form of a grip that is pivotally coupled to the housing 222 and a spring 242 biases the actuator 226 away from the housing 222. The actuator 226 is operatively coupled to the tensioning unit 228 via a pawl (not shown) such that when the actuator 226 is actuated, e.g., gripped or squeezed such that a force is exerted against the spring 242), the actuator 226 causes the pawl to move (e.g., rotate) a strap mount 244 (see FIGS. 5 and 6) of the tensioning unit 228. For example, when the actuator 226 is actuated, the strap mount 244 rotates clockwise. As described above, the traveler strap 234 of the catheter assembly 230 can be coupled to the handle assembly 220 such that the traveler strap 234 engages the strap mount 244 of the tensioning unit 228 as shown in FIG. 6. A retention member 231 is used to hold and maintain the traveler strap 234 coupled to the handle assembly 220. The retention member 231 can be rotated as shown in FIGS. 5 and 6 to provide access to the strap mount 244 and insert the traveler strap 234 to engage teeth 245 on the strap mount 244 (as shown in FIG. 6). In some embodiments, the traveler strap 234 engages the strap mount 244 with a friction fit. In some embodiments, the traveler strap 234 includes teeth (not shown) along at least a portion of a length of the traveler strap 234 that engage teeth 245 on the strap mount 244. Thus, the tensioning unit 228 can function as a ratcheting mechanism to pull the handle assembly 220 distally along traveler strap 234 with each actuation of the actuator 226.

Figure 9:
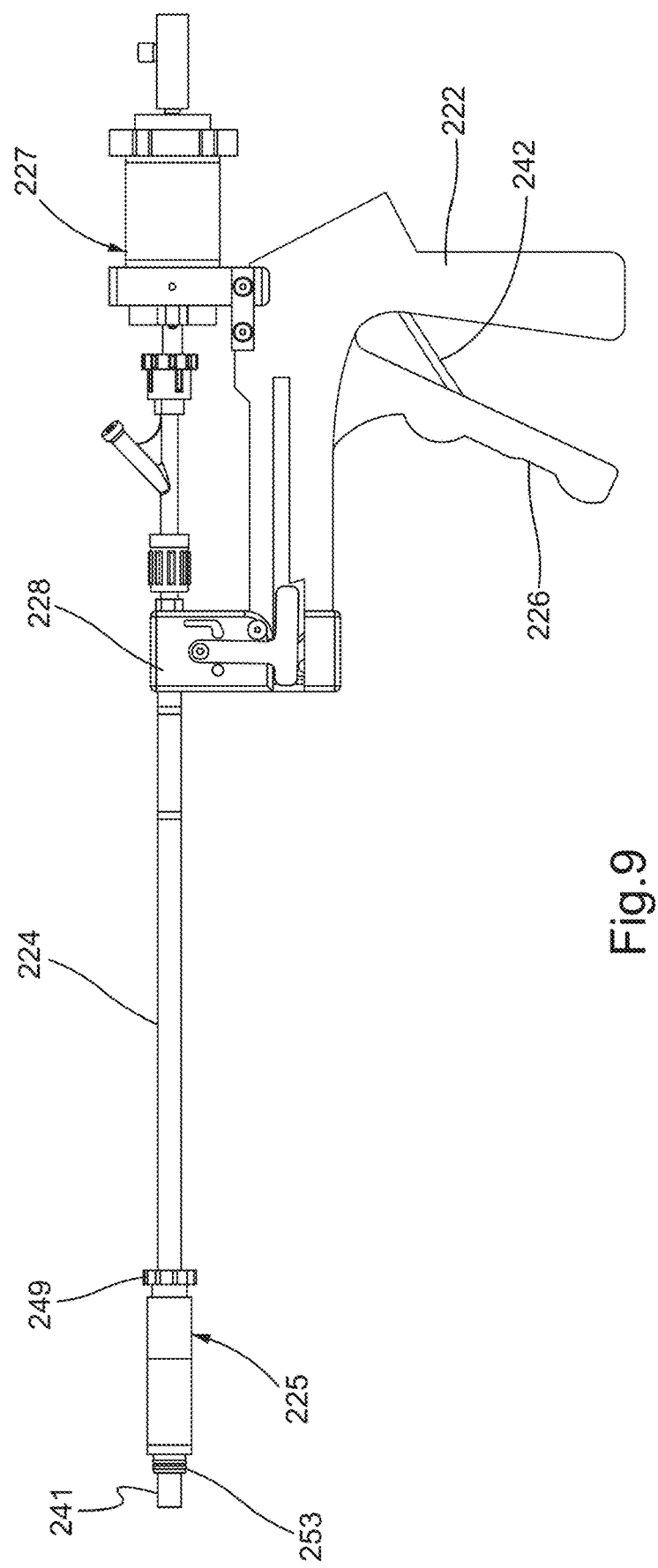
FIG. 9 is a side view of the handle assembly of FIG. 4 with the valve loading tube of FIG. 8 coupled to a distal end portion thereof.

The valve holding tube 225 (see, e.g., FIGS. 8 and 9) can contain or hold a prosthetic mitral valve (not shown) in a compressed configuration within an interior lumen 246 of the valve holding tube 225. As described in more detail below, a valve loading device (see, e.g., FIGS. 12-14) can be used to load the prosthetic valve into the valve holding tube 225 such that the prosthetic valve is compressed to a desired size and shape in a controlled manner. The valve holding tube 225 (with the prosthetic mitral valve therein) can be coupled to a distal end portion of the elongate shaft 224 of the handle assembly 220 as shown in FIG. 9. For example, a portion of the distal end portion of the elongate shaft 224 of the handle assembly 220 can be received through a proximal opening 248 of a cap member 249 and within the interior region 246 such that a distal end of the elongate shaft 224 is disposed proximal of the prosthetic valve within the valve holding tube 225. Prior to coupling the valve holding tube 225 to the elongate shaft 224, a tether (not shown) coupled to the prosthetic valve (within the valve holding tube 225) can be threaded through a lumen defined by the elongate shaft 224, through the positioner 227 and extend proximally out of the handle assembly 220. The valve holding tube 225 also includes markings 257 and 259 that can be used to align to corresponding marks (not shown) on the distal end portion of the elongate shaft 224 of the handle assembly 220. The valve loading tube 225 also includes o-rings 253 on a distal end portion 241 (see FIG. 8) of the valve holding tube 225 that can be used to hold the valve holding tube 225 within the interior region 238 of the hub 232 of the catheter assembly 230.

As described above for the previous embodiment, the valve holding tube 225 can have various lengths to accommodate various different procedures to deliver the prosthetic heart valve to the heart. For example, in some embodiments, the valve holding tube 225 can have a length of between about 10 cm and 150 cm. In some embodiments, the valve holding tube 225 can have a length of about 12 cm to about 38 cm. In some embodiments, the valve holding tube 225 can have a length of about 50 cm to about 150 cm.

The positioner 227 is mounted to a proximal end portion of the housing 222. A set screw(s) 247 can be used to secure the positioner 227 to the housing 222. The positioner 227 can be used to fine tune the advancement or deployment of the mitral valve within the catheter assembly 230 and into the heart. As described above, one or more tethers coupled to the prosthetic valve can be passed or threaded through a lumen of the positioner 227 and extend out an opening 233 (see FIG. 4). A vise (not shown) within the positioner 227 can be tightened around the tether to lock it in place. The positioner 227 includes a wheel or dial 250 that when turned extends a center tube 251 proximally out of the positioner 227. The center tube 251 can include deployment distance markings (not shown) that can be used to inform the user how far the prosthetic valve has been advanced during deployment. The markings can be, for example, labeled with numbers or letters, or can be color coded. To deploy the prosthetic valve, the dial is rotated counterclockwise and to reposition the valve the dial is rotated clockwise. The tether can be tightened using a slight rotation clockwise.

Figure 10:
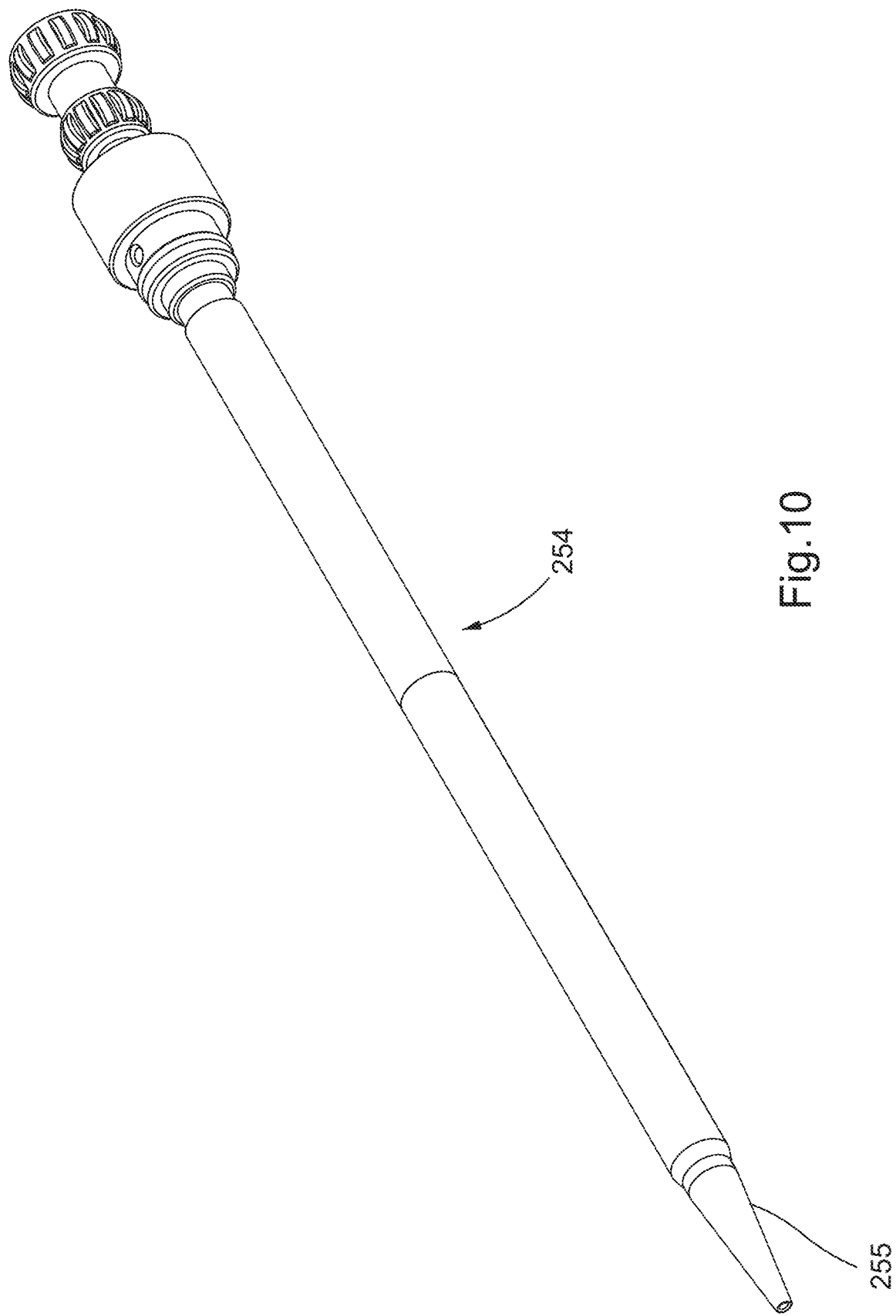
FIG. 10 is a perspective view of a dilator device, according to an embodiment.
Figure 11:
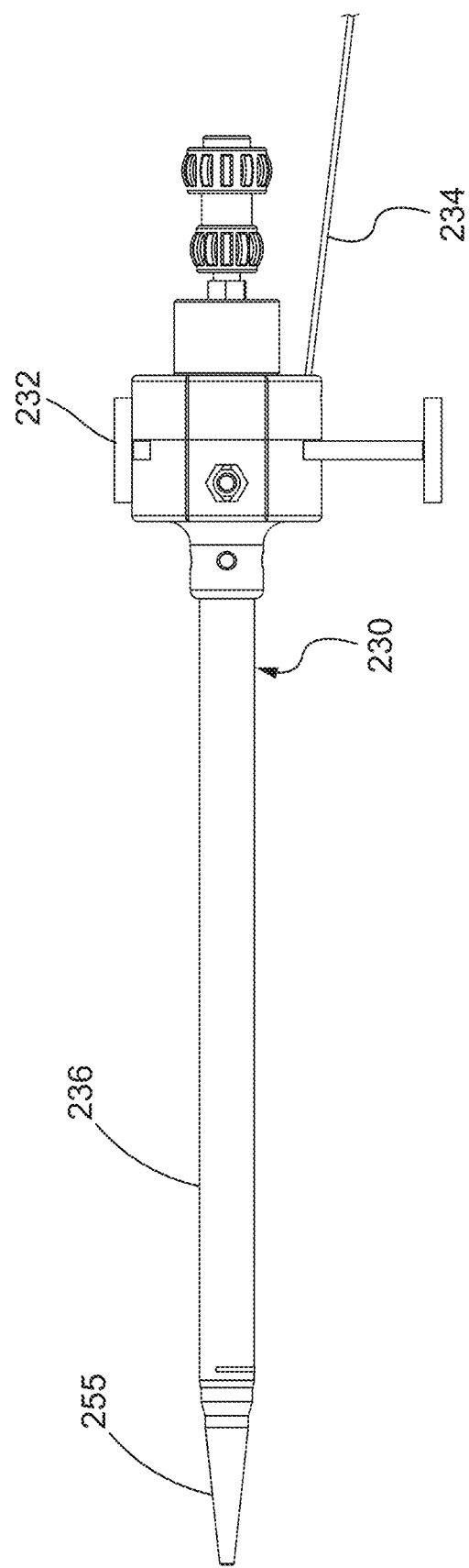
FIG. 11 is a side view of the catheter assembly of FIG. 7 with the dilator device of FIG. 10 coupled thereto.

To deliver and deploy the prosthetic mitral valve within a heart, the sheath 236 of the catheter assembly 230 is inserted through the epicardial surface of heart and extended through the left ventricle and to the left atrium of the heart such that the hub 232 is disposed on the outside of the heart near or in contact with the epicardial surface. In some embodiments, prior to introducing the sheath 236 into the heart, a guidewire is extended into the heart and to the left atrium. The sheath 236 can then be threaded over the guidewire. In some embodiments, prior to inserting the sheath 236 into the heart, a dilator device 254 (see FIGS. 10 and 11) can be inserted through the hub 232 and through the lumen of the sheath 236, such that a tapered distal end portion 255 of the dilator device 254 extends outside a distal end of the sheath 236. The tapered distal end portion 255 of the dilator device 254 can provide a lead-in for the sheath 236 and help open or enlarge the entry opening at the epicardial surface and through the mitral annulus. When the sheath 236 is placed at the desired position within the heart, the dilator device 254 can be removed leaving the sheath 236 within the heart.

Figure 3:
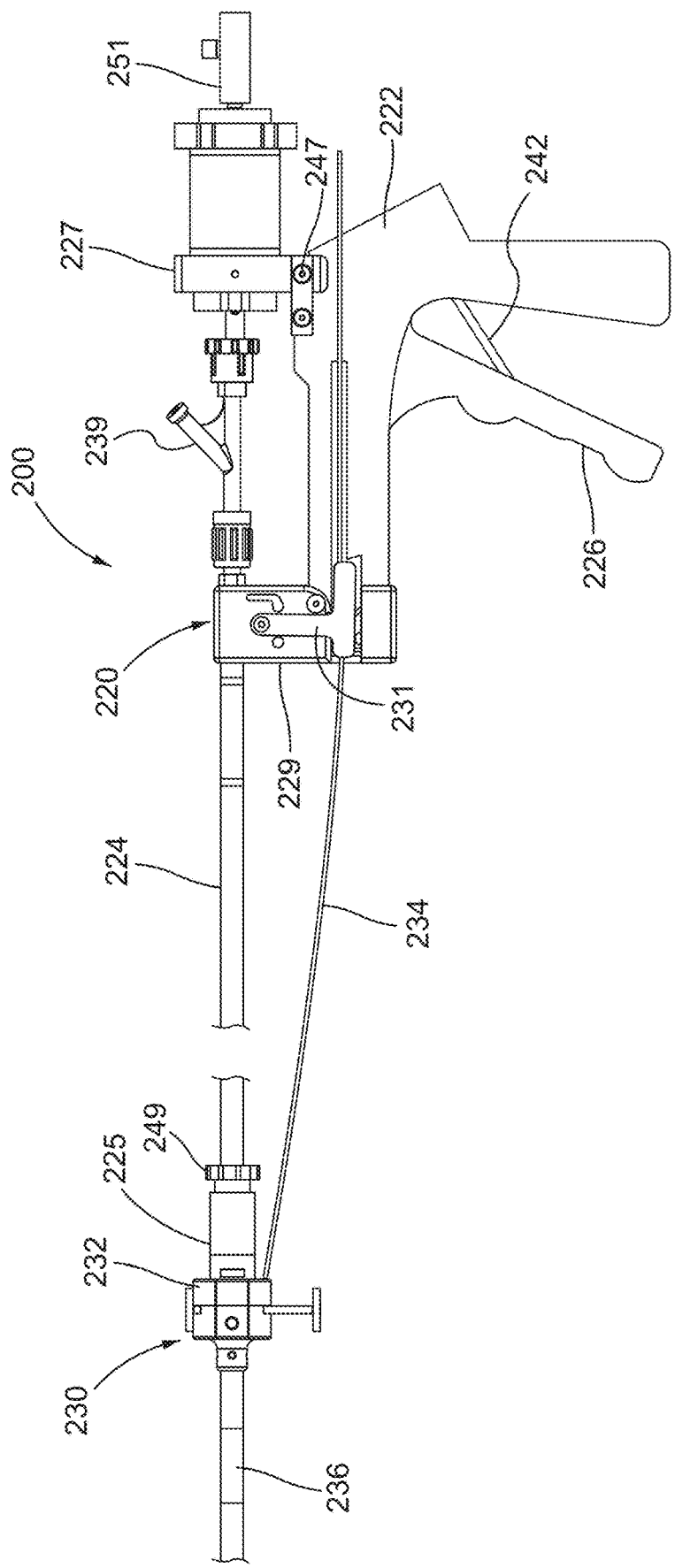
FIG. 3 is a side view of a portion of a delivery device, according to an embodiment.
Figure 4:
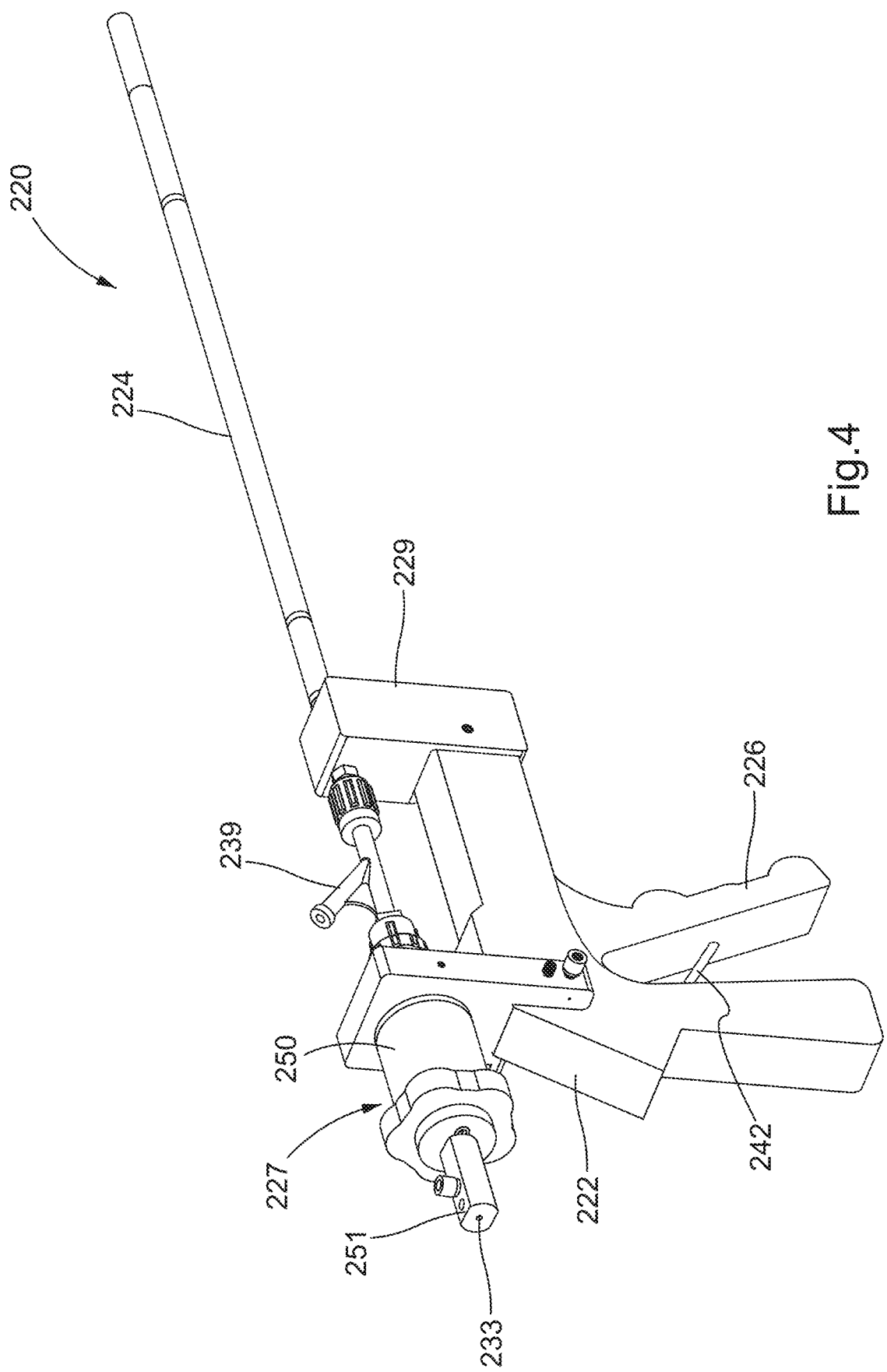
FIG. 4 is a perspective view of a handle assembly of the delivery device of FIG. 3.

With the valve holding tube 225 coupled to the distal end portion of the elongate shaft 224 of the handle assembly 220, the traveler strap 234 of the catheter assembly 230 can be coupled to the strap mount 244 of the tensioning unit 228 of the handle assembly 220 (as shown in FIGS. 3 and 6). The distal end portion 241 of the valve holding tube 225 can then be inserted into the interior region 238 of the hub 232 and the o-rings 253 can secure the valve holding tube 225 in a stationary or fixed position within the lumen 238 of the hub 232 (as shown in FIG. 3). The actuator 226 of the handle assembly 220 can then be actuated by squeezing the actuator grip toward the housing 222 of the handle assembly 220 to cause the tensioning unit 228 to pull or move the handle assembly 220 distally. As the handle assembly 220 moves distally, a distal end of the elongate shaft 224 of the handle assembly 220 pushes the prosthetic mitral valve out of the valve holding tube 225, into the lumen 237 of the sheath 236 of the catheter assembly 230 and eventually out a distal end of the sheath 236 and into the left atrium of the heart. As the prosthetic mitral valve is released with the heart, and is no longer contained within the valve holding tube 225 or the sheath 236, the prosthetic mitral valve can assume an expanded configuration. Each actuation of the actuator 226 incrementally moves the handle assembly 220, providing a controlled incremental release of the prosthetic mitral valve within the heart. As described above, the positioner 227 can be used to control the rate of deployment of the prosthetic valve and/or can be used to reposition the valve as needed.

Figure 12:
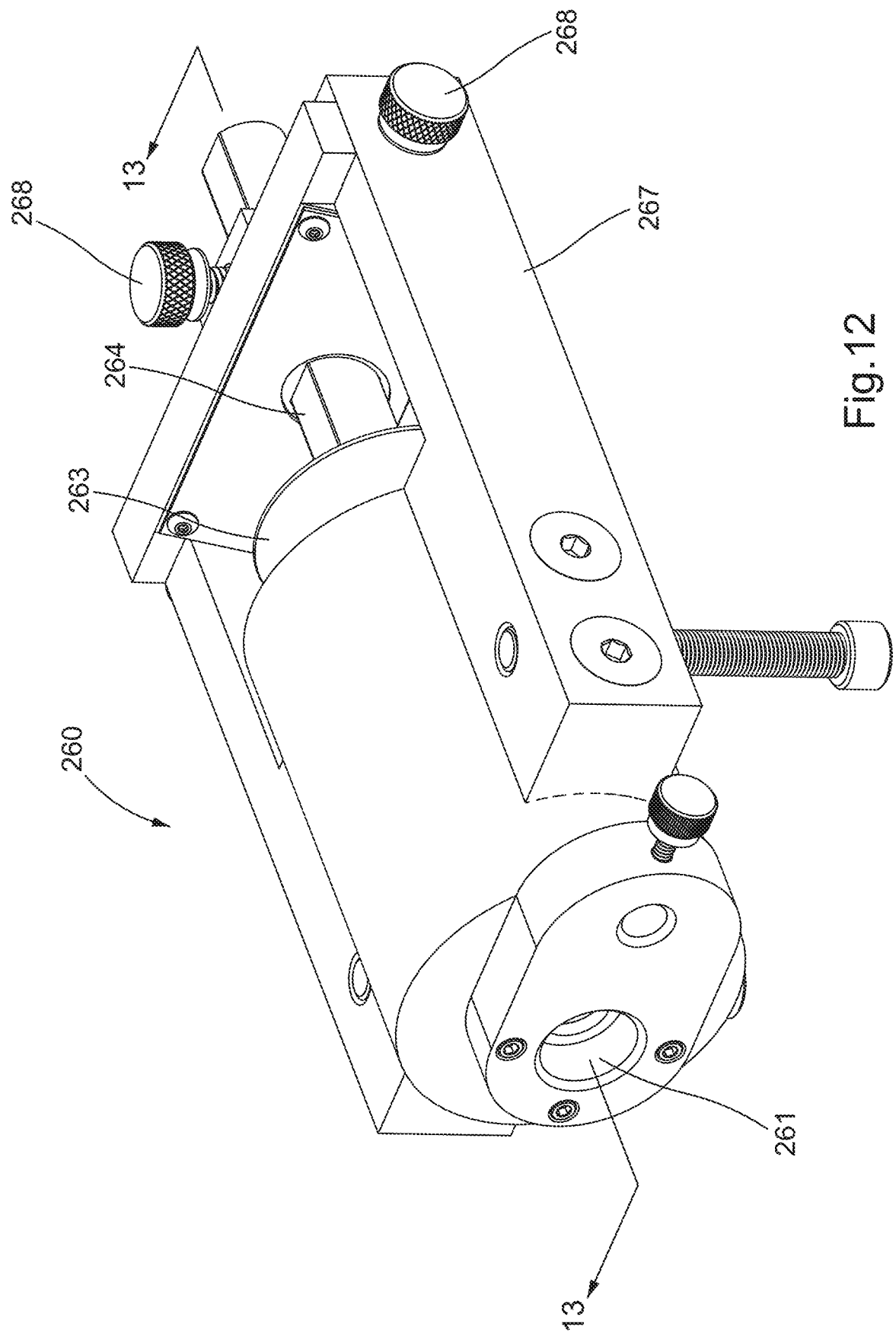
FIG. 12 is a perspective view of a valve loading device, according to an embodiment.
Figure 13:
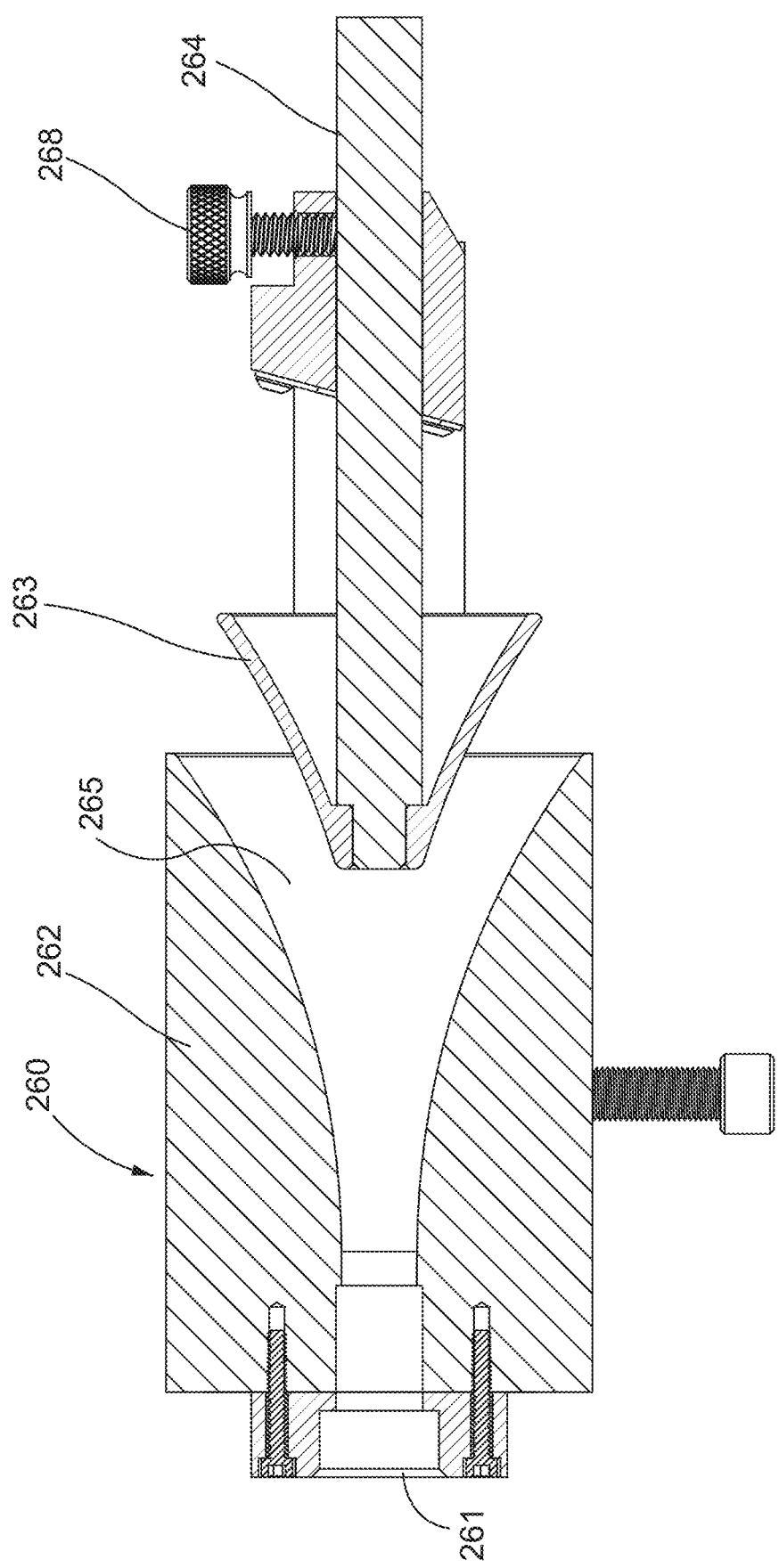
FIG. 13 is a cross-sectional view of the valve loading device of FIG. 12 taken along line 13-13 in FIG. 12.
Figure 14:
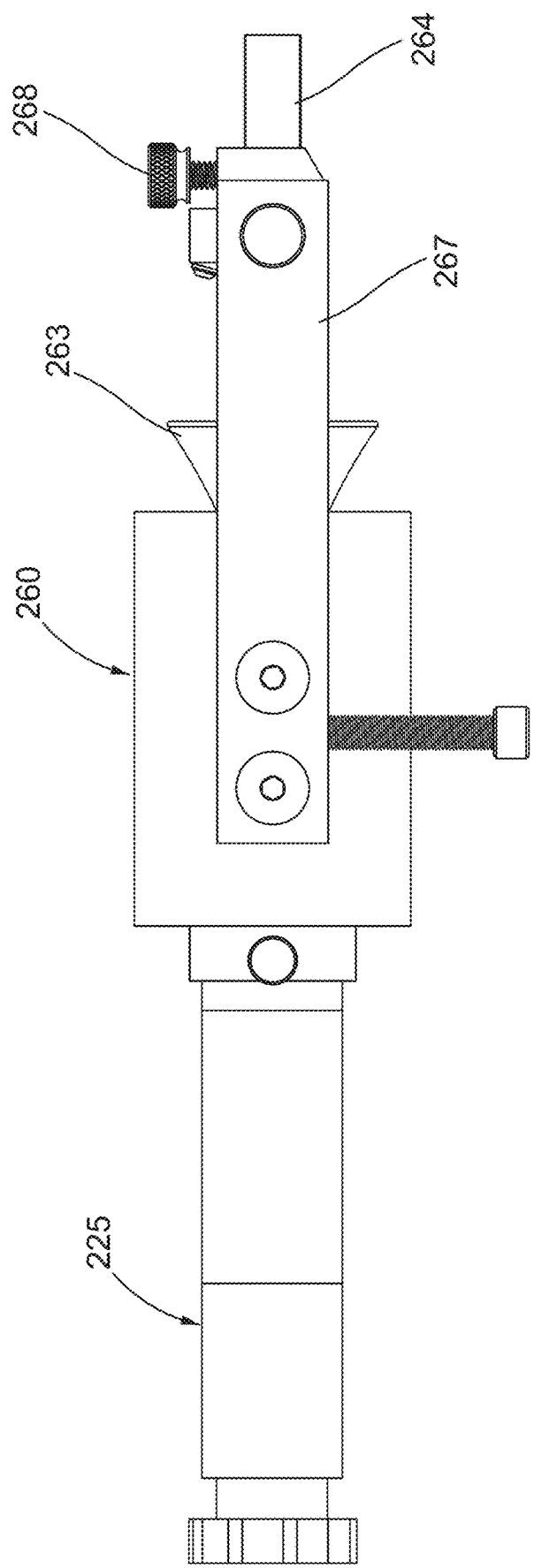
FIG. 14 is a side view of the valve holding tube of FIG. 8 coupled to the valve loading device of FIG. 12.

FIGS. 12-14 illustrate a valve loading device 260 that can be used to compress the prosthetic valve to a desired size and shape prior to loading the valve into the valve holding tube 225. The valve loading device 260 includes an inner funnel 262, a removable outer funnel 263 and a removable centering tube 264. The outer funnel 263 and centering tube 264 can be removably coupled to the inner funnel 262 via a bracket assembly 267. The bracket assembly 267 can be coupled and uncoupled from the outer funnel 262 using bolts or screws 268.

The process of loading the prosthetic valve into the valve loading device 260 (also referred to as "loading device") should be performed with the valve and loading device 260 submerged in a saline/water bath with care being taken to remove all trapped air bubbles within the loading device 260. The outer funnel 263 and centering tube 264 are removed from the inner funnel 262. The prosthetic heart valve can be placed within a larger diameter area of an interior region 265 defined by the inner funnel 262 (shown in FIG. 13). The tether of the valve is threaded through the inner funnel 262. In some embodiments, with an asymmetric prosthetic mitral valve, the valve is loaded into the loading device 260 so that the A2 section of the valve (see PCT application '58826) is loaded upwards. This can ensure that the A2 segment of the valve is compressed in the same way it is delivered to the A2 region of the anterior native leaflet to reduce or prevent LVOT obstruction.

The outer funnel 263 and centering tube 264 can then be coupled to the inner funnel 262 and the centering tube 264 to hold the prosthetic valve in position within the interior region 265. For example, the centering tube 264 can be inserted through a center of the valve and through a center of the outer funnel 263 and inner funnel 262. The valve can be checked for air, shaken, tapped to remove trapped air, etc. while within the loading device 260. If any bubbles are seen, they can be removed with a syringe, especially out of any top pockets of the valve.

Next, the handle assembly 220 can be used to draw or move the prosthetic valve from the valve loading device 260 to the valve holding tube 225. For example, the valve loading tube 225 can be coupled to an exit end of the valve loading device 260 as shown in FIG. 14. A load assist device 269 can be coupled between the handle assembly 220 and the valve holding tube 225, as shown in FIGS. 15 and 16.

The load assist device 269 secures the valve holding tube 225 and valve loading device 260 in a fixed relation to the handle assembly 220. The tether 275 (as shown in FIGS. 15 and 16) of the prosthetic valve (disposed within the loading device 260 in FIG. 15 and within the valve holding tube 225 in FIG. 16) can be threaded through the lumen of the valve holding tube 225 and coupled to a first bracket 271 of the load assist device 269. For example, a piercing pin can be used to secure the tether 275 to the first bracket 271. The load assist device 269 includes a load assist strap 277 also coupled to the first bracket 271. A second bracket 273 can be used to hold the valve holding tube 225. For example, the second bracket 273 can define a groove or cut-out that can receive the valve holding tube 225.

With the load assist strap 277 engaged with the tensioning unit 228 of the handle assembly 220, the handle assembly 220 can be actuated in the same manner as described above (e.g., by gripping or squeezing the actuator 226), which will draw the load assist strap 277 toward the handle assembly 220 pulling the first bracket 271 with it. Thus, the first bracket 271 can be moved from a first position (closer to the second bracket 273), as shown in FIG. 15 to a second position (closer to the handle assembly 220) as shown in FIG. 16. Because the tether 275 is coupled to the first bracket 271, the movement of the first bracket 271 pulls the tether 275, and thus, pulls the prosthetic valve toward the handle assembly 220 and out of the valve loading device 260 and into the valve holding tube 225. With the valve disposed within the valve holding tube 225, the load assist device 269 can be decoupled from the handle and from the valve holding tube 225.

Figure 17A:
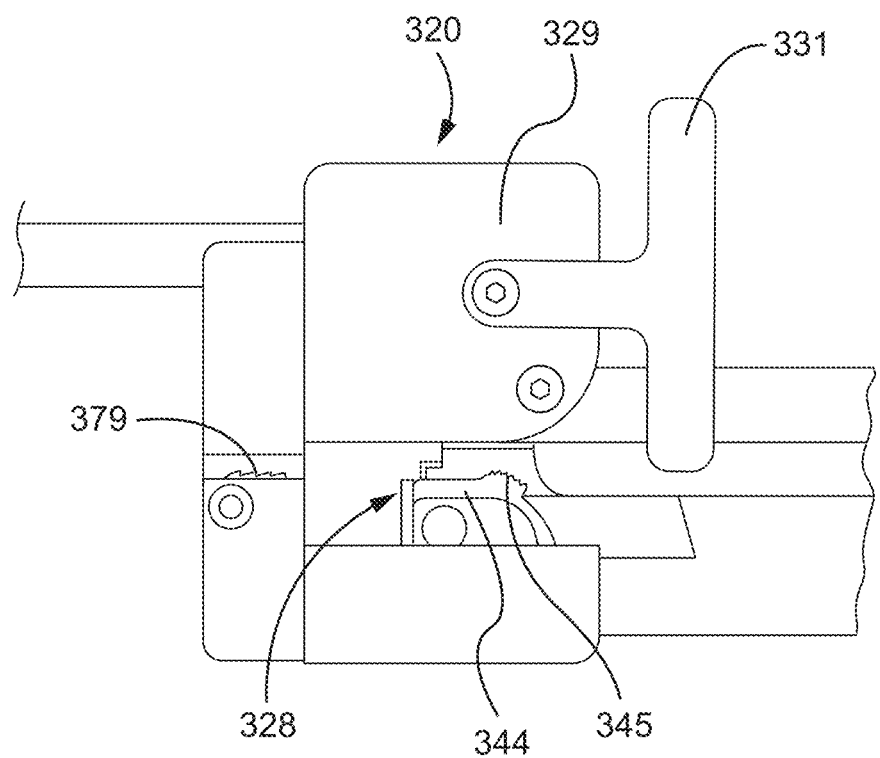
FIGS. 17A and 17B are enlarged side views of a portion of a handle assembly according to another embodiment.
Figure 17B:
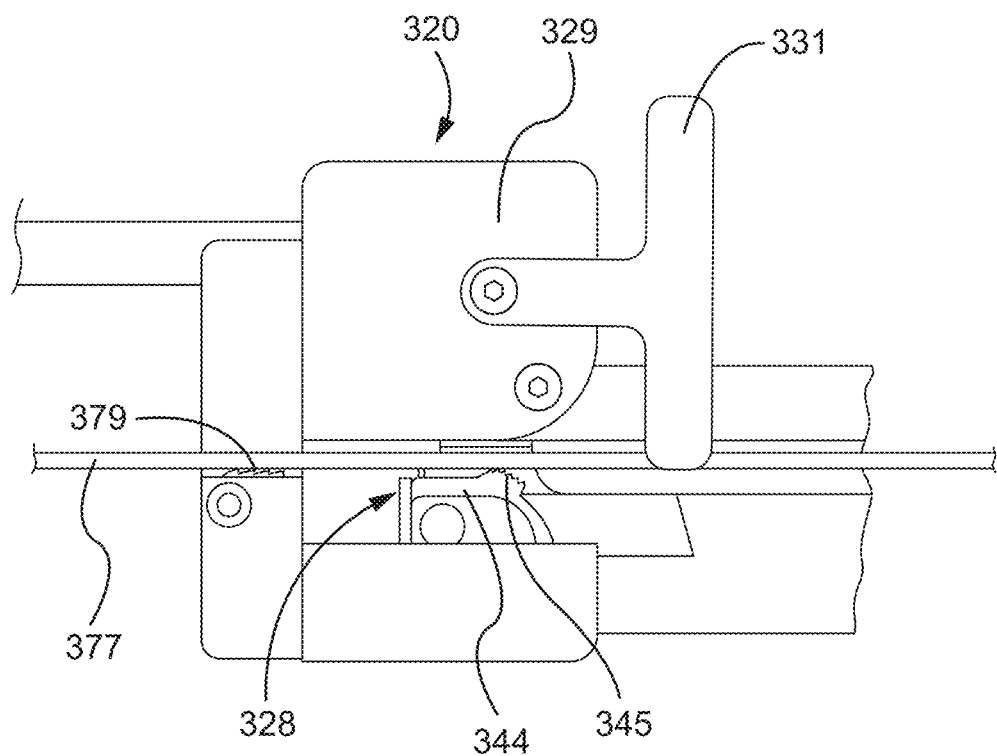

FIGS. 17A and 17B illustrate a portion of an alternative embodiment of a handle assembly that can be used to move the prosthetic valve from the loading device 260 to the valve holding tube 225. A handle assembly 320 can be constructed the same as or similar to the handle assembly 220. Only those portions that vary are discussed here. The handle assembly 320 includes a modified coupling block 329 and tensioning unit 328. The tensioning unit 328 includes a strap mount 344 similar to the strap mount 244 and can be actuated in a similar manner as described for handle assembly 220. The strap mount 344 includes teeth 345 that can engage a load assist strap 377 of a load assist device such as load assist device 269 described above. In this embodiment, the coupling block 329 also includes teeth 379 that can engage the load assist strap 377 (shown in FIG. 17B) of the load assist device. The teeth 379 provide for movement of a load assist device in only one direction. As with the previous embodiment, a retention member 331 can be rotated to gain access to load or insert the load assist strap 377.

Figure 18:
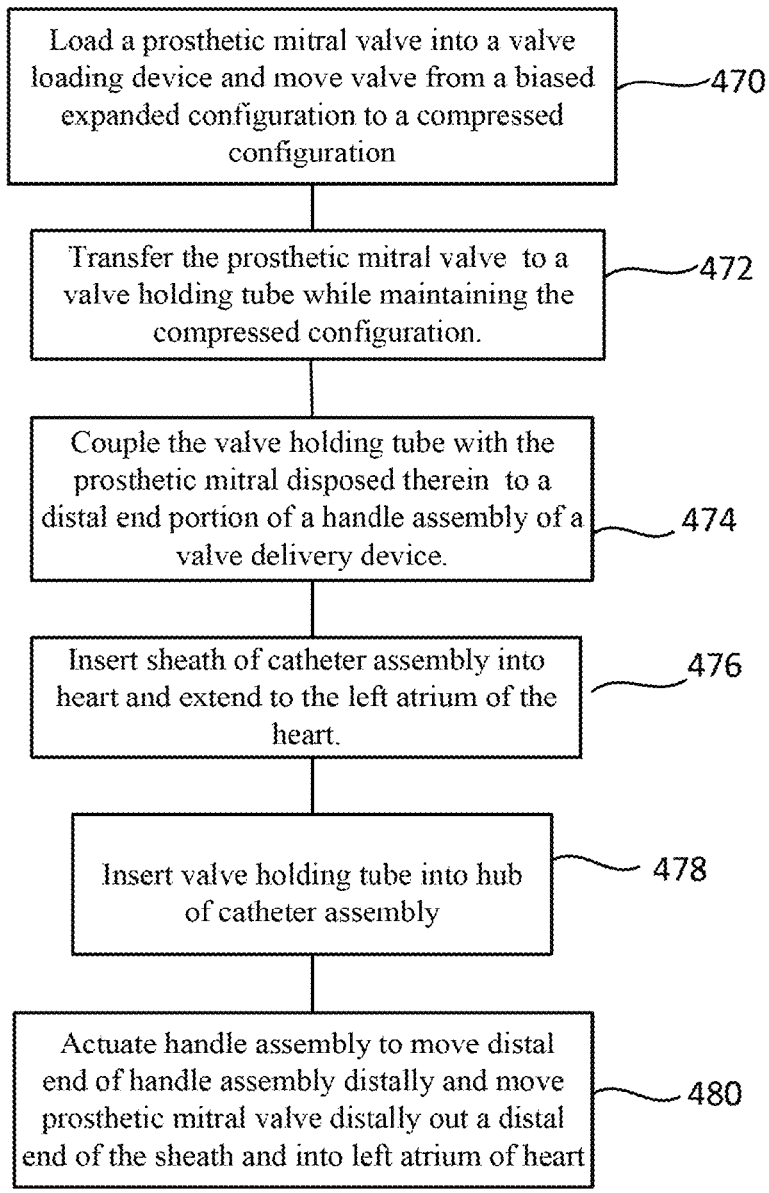
FIG. 18 is a flowchart of a method of delivering and deploying a prosthetic mitral valve to a heart.

FIG. 18 is a flowchart illustrating a method of deploying a prosthetic mitral valve into a heart, according to an embodiment. At 470, a prosthetic mitral valve is loaded into a valve loading device and moved from a biased expanded configuration to a compressed configuration within the valve loading device. At 472, the prosthetic mitral valve is transferred to a valve holding tube while maintaining the compressed configuration. At 474, the valve holding tube with the prosthetic mitral disposed therein in a compressed configuration is coupled to a distal end portion of a handle assembly of a valve delivery device. In some embodiments, prior to coupling the valve holding tube to the distal end of the handle assembly, a tether coupled to the prosthetic mitral valve is threaded through a lumen of the handle assembly and through a lumen of a positioning device of the handle assembly. The positioning device can be used to hold the tether and control movement of the prosthetic mitral valve during deployment into the heart. For example, a dial on the positioning device can be moved or rotated to adjust a tension on the tether extending through the positioning device. At 476, a sheath of a catheter assembly is inserted into a heart and extended to the left atrium of the heart. At 478, after inserting the sheath of the catheter assembly into the heart, the valve holding tube (while coupled to the distal end of the handle assembly) is inserted partially into the hub of the catheter assembly which extends outside of the heart. At 480, the handle assembly is actuated such that the handle assembly is moved distally and a distal end of the handle assembly moves the prosthetic mitral valve distally out of the valve holding tube and out a distal end of the sheath and into the left atrium of the heart. The prosthetic mitral valve is moved to a biased expanded configuration within the heart when uncompressed within the holding tube and sheath. In some embodiments, the handle assembly includes an actuator coupled to a tensioning unit, the catheter assembly includes a traveler strap configured to be coupled to the tensioning unit, and the actuation of the handle assembly includes actuating the actuator such that the tensioning unit pulls the handle assembly distally along the traveler strap.

Figure 19:
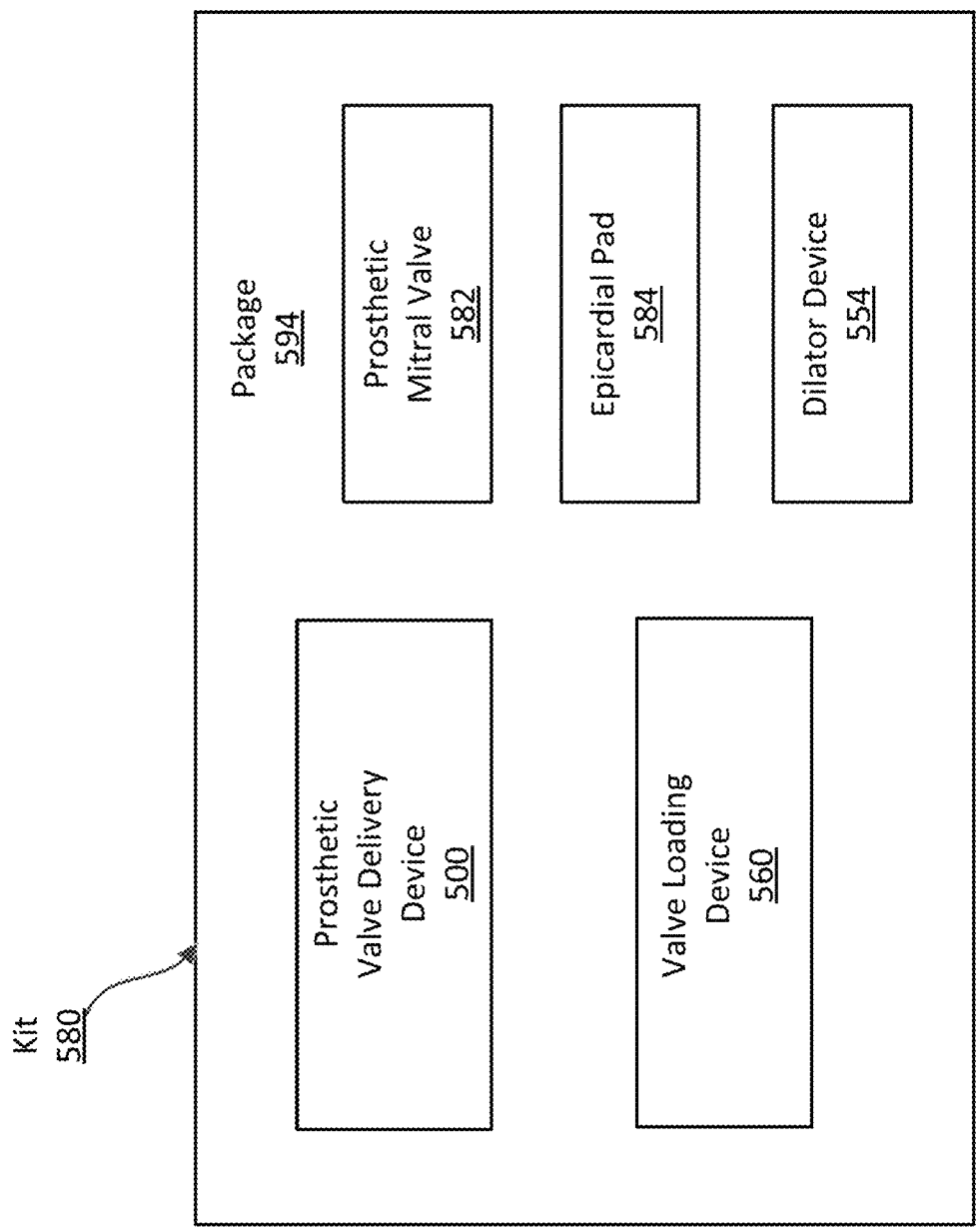
FIG. 19 is a schematic illustration of a surgical kit for delivering and deploying a prosthetic mitral valve, according to an embodiment.

FIG. 19 is a schematic illustration of a kit according to an embodiment. In some embodiments, a surgical kit 580 can include a delivery device 500 which can be, for example, a delivery device as described herein (e.g., delivery device 100, 200) and a valve loading device 560. A kit can optionally include one or more of a transcatheter prosthetic valve 582 (e.g., a prosthetic mitral valve) and/or an epicardial pad 584 to secure the transcatheter valve 582 in position within the heart and/or a dilator device 554 as described herein and/or a guidewire (not shown in FIG. 19). A kit can also include a sterile package in which the components of the kit can be sealed for transport.

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above Where schematics and/or embodiments described above indicate certain components arranged in certain orientations or positions, the arrangement of components may be modified. While the embodiments have been particularly shown and described, it will be understood that various changes in form and details may be made. Any portion of the apparatus and/or methods described herein may be combined in any combination, except mutually exclusive combinations. The embodiments described herein can include various combinations and/or sub-combinations of the functions, components, and/or features of the different embodiments described.

The invention claimed is:

1. An apparatus, comprising:
a catheter assembly including a sheath;
a handle assembly operably coupled to the sheath, the handle assembly including a shaft and an actuator;
a positioning device; and
a prosthetic heart valve configured to be received within the sheath in a collapsed configuration, the prosthetic heart valve including a tether configured to be received within the positioning device;
wherein the actuator, when actuated, is configured to advance the prosthetic heart valve distally relative to the sheath, and the positioning device, when the tether is secured within the positioning device, is configured to restrict movement of the prosthetic heart valve relative to positioning device.

2. The apparatus of claim 1, wherein the positioning device is configured to be fixedly mounted to the handle assembly.

3. The apparatus of claim 2, wherein the positioning device includes a vise that can be tightened to lock the tether to the positioning device.

4. The apparatus of claim 1, wherein the positioning device includes a dial rotatable in a first direction to draw the tether proximally relative to the sheath.

5. The apparatus of claim 4, wherein the dial is rotatable in a second direction opposite the first direction to allow the tether to advance distally relative to the sheath.

6. The apparatus of claim 5, wherein the positioning device includes a tube configured to be secured to the tether, and rotation of the dial in the first direction moves the tube proximally, while rotation of the dial in the second direction advances the tube distally.

7. The apparatus of claim 6, wherein the tube includes deployment distance markings that correspond to a distance which the prosthetic heart valve has been advanced during a deployment procedure.

8. The apparatus of claim 1, wherein the actuator, when actuated, is configured to advance the shaft distally within the sheath.

9. The apparatus of claim 8, wherein when the prosthetic heart valve is received within the sheath in the collapsed configuration, a distal end of the shaft is adapted to abut a proximal end of the prosthetic heart valve.

10. The apparatus of claim 9, wherein the tether is coupled to the proximal end of the prosthetic heart valve and is configured to extend through a lumen in the shaft to a lumen in the positioning device.

11. A method of deploying a prosthetic heart valve, the method comprising:
inserting a sheath of a catheter into a heart of a patient;
actuating an actuator of a handle assembly to drive a shaft of the handle assembly distally through the sheath;
wherein, driving the shaft of the handle assembly distally through the sheath drives a prosthetic heart valve distally through the sheath, the prosthetic heart valve received within the sheath in a collapsed configuration;
wherein, while the prosthetic heart valve is driven distally through the sheath, a tether coupled to the prosthetic heart valve is received within a positioning device so as to restrict movement of the prosthetic heart valve relative to positioning device.

12. The method of claim 11, further comprising tightening a vise of the positioning device to lock the tether to the positioning device prior to driving the prosthetic heart valve distally through the sheath.

13. The method of claim 11, further comprising rotating a dial of the positioning device in a first direction to begin deploying the prosthetic heart valve out of the distal end of the sheath into the heart of the patient.

14. The method of claim 13, further comprising rotating the dial of the positioning device in a second direction opposite the first direction to begin drawing the prosthetic heart valve back into the sheath.

15. The method of claim 14, wherein rotation of the dial in the first direction moves a tube of the positioning device distally, the tether being secured to the tube.

16. The method of claim 15, wherein the tube includes deployment distance markings that correspond to a distance which the prosthetic heart valve has been advanced during a deployment procedure.

17. The method of claim 11, wherein the tether is coupled to the proximal end of the prosthetic heart valve and extends through a lumen in the shaft to a lumen in the positioning device while the prosthetic heart valve is driven distally through the sheath.

18. The method of claim 11, wherein actuating the actuator pulls a strap proximally relative to the handle assembly, a distal portion of the strap being operably coupled to the sheath.

19. The method of claim 18, wherein pulling the strap proximally relative to the handle assembly advances the shaft distally relative to the sheath.

20. The method of claim 11, further comprising:
- inserting the prosthetic heart valve into an interior region of a valve loading device while in a biased expanded configuration;
- moving the prosthetic heart valve from the biased expanded configuration to the collapsed configuration while disposed within the valve loading device;
- transferring the prosthetic heart valve while in the compressed configuration from the valve loading device to a valve holding tube; and
- coupling the valve holding tube with the prosthetic heart valve disposed therein in the compressed configuration to a distal end of the shaft prior to driving the prosthetic heart valve distally through the sheath.

* * * * *